US009670250B2

(12) United States Patent
Greenbaum

(10) Patent No.: US 9,670,250 B2
(45) Date of Patent: Jun. 6, 2017

(54) ALPHA-HELICAL PEPTIDOMIMETIC INHIBITORS AND METHODS USING SAME

(71) Applicant: The Trustees of the University of Pennsylvania, Philadelphia, PA (US)

(72) Inventor: Doron C. Greenbaum, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/397,334

(22) PCT Filed: Apr. 26, 2013

(86) PCT No.: PCT/US2013/038448
§ 371 (c)(1),
(2) Date: Oct. 27, 2014

(87) PCT Pub. No.: WO2013/163567
PCT Pub. Date: Oct. 31, 2013

(65) Prior Publication Data
US 2015/0133367 A1    May 14, 2015

Related U.S. Application Data

(60) Provisional application No. 61/639,552, filed on Apr. 27, 2012.

(51) Int. Cl.
| | |
|---|---|
| *C07K 7/08* | (2006.01) |
| *C07K 7/06* | (2006.01) |
| *H01R 13/73* | (2006.01) |
| *H01R 9/22* | (2006.01) |
| *H01M 2/10* | (2006.01) |
| *H01M 2/20* | (2006.01) |
| *H01M 2/34* | (2006.01) |
| *H01M 10/42* | (2006.01) |
| *H01M 10/48* | (2006.01) |
| *H01R 13/684* | (2011.01) |

(52) U.S. Cl.
CPC .............. *C07K 7/08* (2013.01); *C07K 7/06* (2013.01); *H01M 2/1077* (2013.01); *H01M 2/206* (2013.01); *H01M 2/34* (2013.01); *H01M 2/348* (2013.01); *H01M 10/425* (2013.01); *H01M 10/486* (2013.01); *H01R 9/226* (2013.01); *H01R 13/73* (2013.01); *H01M 2220/20* (2013.01); *H01R 13/684* (2013.01)

(58) Field of Classification Search
CPC ......... C07K 7/08; C07K 7/06; H01M 2/1077; H01M 2/206; H01M 2/34; H01M 2/348; H01M 10/425; H01M 10/486; H01R 9/226; H01R 13/73; H01R 2220/20; H01R 13/684
See application file for complete search history.

(56) References Cited

U.S. PATENT DOCUMENTS

2010/0286365 A1* 11/2010 Ghosh .............. A61K 47/48061
                                                        530/324
2014/0357577 A1* 12/2014 Malcolm .............. C07K 14/005
                                                        514/21.3

FOREIGN PATENT DOCUMENTS

| EP | 0468714 | 1/1992 |
| WO | 95/23222 | 8/1995 |
| WO | 2009/124265 | 10/2009 |

OTHER PUBLICATIONS

Pace and Scholtz, Biophys. Jl., vol. 75, Jul. 1998, 422-427.*
Khan et al., Serpin Inhibition Mechanism: A Delicate Balance between Native Metastable State and Polymerization, J. Amino Acids, 2011, pp. 1-10.*
Luke et al. An Intracellular Serpin Regulates Necrosis by Inhibiting the Induction and Sequelae of Lysosomal Injury, Cell 130, 1108-1119, Sep. 21, 2007.*
Al-Omari et al., Acute-Phase Protein α-Antitrypsin Inhibits Neutrophil Calpain I and Induces Random Migration, Mol. Med. 17;9-10, pp. 865-874, Sep.-Oct. 2011.*
Abstract of Brantly et al., Molecular Basis of alpha-1-antitrypsin deficiency, Am J Med. Jun. 24, 1988;84(6A):13-31.*
Pandey et al., Regulatory elements within the Prodomain of Falcipain-2, a Cysteine Protease of the Malaria Parasite Plasmodium falciparum, PLos ONE, May 2009, vol. 4, issue 5, pp. 1-9.*
Korde, A Prodomain Peptide of Plasmodium falciparum Cysteine Protease (Falcipain-2) Inhibits Malaria Parasite Development, J. Med. Chem., 51, 3116-3123 (2008).*
Fujimoto et al., Development of a Series of Cross-Linking Agents that Effectively Stabilize a-Helical Structures in Various Short Peptides, Chem Eur. J. 2008, 14, 857-863.*
Rousch et al., Potent Second Generation Vinyl Sulfonamide Inhibitors of the Trypanosomal Cysteine Protease Cruzain, Bioorganic& Medicinal Chemistry Letters 11 (2001) 2759-2762.*
Biol Chem. Jun. 2004;385(6):465-72.Interaction of calpastatin with calpain: a review, Wendt A, Thompson V.F., Goll D.E.*
Forkey et al., Protein structural dynamics by single-molecule fluorescence polarization, Progress in Biophysics & Molecular Biology, 2000, vol. 74. pp. 1-35.
Griffin et al., Specific Covalent Labeling of Recombinant Protein Molecules Inside Live Cells, Science, 1998, vol. 281., pp. 269-272.
Podobnik, et al., Crystal structure of the wild-type human procathepsin B at 2.5 A resolution reveals the native active site of a papain-like cysteine protease zymogen, 1997, J Mol Biol 271:774-788.

(Continued)

Primary Examiner — Karlheinz R Skowronek
Assistant Examiner — Joseph Fischer
(74) *Attorney, Agent, or Firm* — Riverside Law LLP

(57) ABSTRACT

The present invention includes a novel class of highly specific protease inhibitors. In one embodiment, the inhibitors of the invention are α-helical in structure. In another embodiment, the present invention represents the first demonstration of a highly specific cysteine protease inhibitor.

2 Claims, 11 Drawing Sheets

(56) References Cited

OTHER PUBLICATIONS

Coulombe, et al., Structure of human procathepsin L reveals the molecular basis of inhibition by the prosegment, 1996, EMBO J 15:5492-5503.

Kaulmann et al., The crystal structure of a Cys25→Ala mutant of human procathepsin S elucidates enzyme-prosequence interactions, 2006, Protein Sci 15:2619-2629.

Henchey, et al., Contemporary strategies for the stabilization of peptides in the α-helical conformation, 2008, Curr Opin Chem Biol 12:692-697.

* cited by examiner

Calpain: IPPKYCEQLC

Cathepsin S: WWEWWCSLMCS

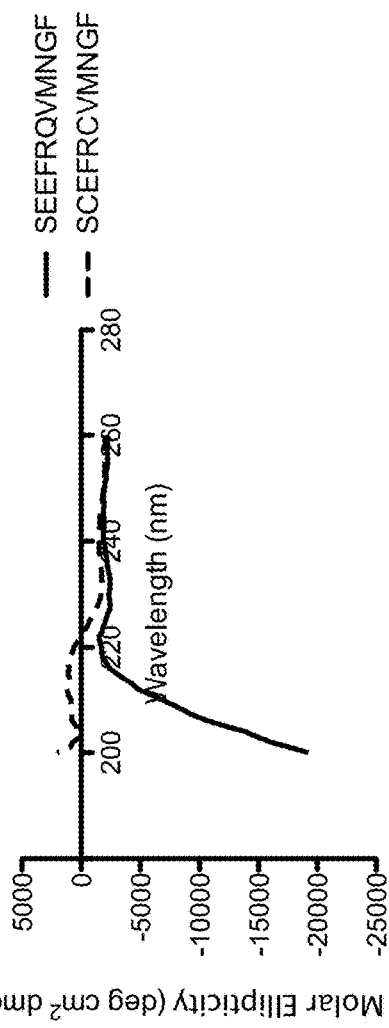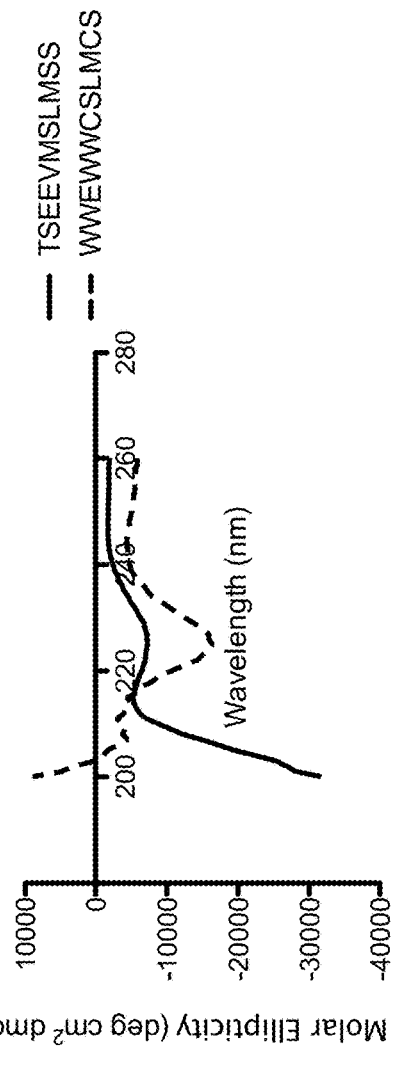

```
                       SEQUENCE LISTING

<160> NUMBER OF SEQ ID NOS: 102

<210> SEQ ID NO 1
<211> LENGTH: 11
<212> TYPE: PRT
<213> ORGANISM: Artificial Sequence
<220> FEATURE:
<223> OTHER INFORMATION: chemically synthesized

<400> SEQUENCE: 1

Ser Glu Glu Phe Arg Gln Val Met Asn Gly Phe
1               5                   10

<210> SEQ ID NO 2
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(3)
<223> OTHER INFORMATION: connected to Cys7 through an alpha,alpha'-
      xylylene linker
<220> FEATURE:
<221> NAME/KEY: MISC_FEATURE
<222> LOCATION: (7)..(7)
<223> OTHER INFORMATION: connected to Cys3 through an alpha,alpha'-
      xylylene linker

<400> SEQUENCE: 2

Ser Glu Cys Phe Arg Gln Cys Met Asn Gly Phe
1               5                   10

<210> SEQ ID NO 3
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 3

Ser Cys Glu Phe Arg Cys Val Met Asn Gly Phe
1               5                   10

<210> SEQ ID NO 4
<211> LENGTH: 11
<212> TYPE: PRT
<213> ORGANISM: Artificial Sequence
```

<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 2-naphthyl alanine
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 4

Ser Cys Glu Xaa Arg Cys Val Met Asn Gly Phe
1               5                   10

<210> SEQ ID NO 5
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenylalanine
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 5

Ser Cys Glu Xaa Arg Cys Val Met Asn Gly Phe
1               5                   10

<210> SEQ ID NO 6
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 6

Ser Cys Glu Phe Arg Cys Val Gln Asn Gly Phe
1               5                   10

<210> SEQ ID NO 7
<211> LENGTH: 11
<212> TYPE: PRT
<213> ORGANISM: Artificial Sequence
<220> FEATURE:
<223> OTHER INFORMATION: chemically synthesized -continued

```
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: 2-naphthyl alanine

<400> SEQUENCE: 7

Ser Cys Glu Phe Arg Cys Val Met Asn Gly Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 8

Ser Cys Glu Phe Ala Cys Val Met Asn Gly Phe
1               5                   10

<210> SEQ ID NO 9
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenylalanine
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: 2-naphthyl alanine

<400> SEQUENCE: 9

Ser Cys Glu Xaa Arg Cys Val Met Asn Gly Xaa
1               5                   10

<210> SEQ ID NO 10
<211> LENGTH: 11
<212> TYPE: PRT
<213> ORGANISM: Artificial Sequence
```

```
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenyl alanine
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: 2-naphthyl alanine

<400> SEQUENCE: 10

Ser Cys Glu Xaa Arg Cys Val Gln Asn Gly Xaa
1               5                   10

<210> SEQ ID NO 11
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenyl alanine
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (10)..(10)
<223> OTHER INFORMATION: d-arginine
<220> FEATURE:
<221> NAME/KEY: MOD_RES
<222> LOCATION: (11)..(11)
<223> OTHER INFORMATION: 2-naphthyl alanine

<400> SEQUENCE: 11

Ser Cys Glu Xaa Arg Cys Val Met Asn Xaa Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenyl alanine
<220> FEATURE:
<221> NAME/KEY: MOD_RES
```

```
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: 2-naphthyl alanine

<400> SEQUENCE: 12

Arg Cys Glu Xaa Gln Cys Val Gln Asn Gly Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenyl alanine
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (10)..(10)
<223> OTHER INFORMATION: d-arginine
<220> FEATURE:
<221> NAME/KEY: MOD_RES
<222> LOCATION: (11)..(11)
<223> OTHER INFORMATION: 2-naphthyl alanine

<400> SEQUENCE: 13

Ser Cys Glu Xaa Arg Cys Val Gln Asn Xaa Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: chemically synthesized

<400> SEQUENCE: 14

Thr Ser Glu Glu Val Met Asn Ser Leu Met Ser Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
```

```
<400> SEQUENCE: 15

Thr Cys Glu Glu Val Cys Ser Leu Met Ser Ser
1               5                   10

<210> SEQ ID NO 16
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 16

Thr Ser Glu Glu Val Cys Ser Leu Met Cys Ser
1               5                   10

<210> SEQ ID NO 17
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 17

Trp Ser Glu Glu Val Cys Ser Leu Met Cys Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 18

Thr Trp Glu Glu Val Cys Ser Leu Met Cys Ser
1               5                   10

<210> SEQ ID NO 19
<211> LENGTH: 11
<212> TYPE: PRT
<213> ORGANISM: Artificial Sequence
```

```
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 19

Thr Ser Ala Glu Val Cys Ser Leu Met Cys Ser
1               5                   10

<210> SEQ ID NO 20
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 20

Thr Ser Glu Trp Val Cys Ser Leu Met Cys Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 21

Thr Ser Glu Glu Trp Cys Ser Leu Met Cys Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
```

```
<223> OTHER INFORMATION: connected to Cys6 through an alpha,alpha'-
      xylylene linker

<400> SEQUENCE: 22

Thr Ser Glu Glu Val Cys Ser Phe Met Cys Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 23

Thr Trp Glu Trp Val Cys Ser Leu Met Cys Ser
1               5                   10

<210> SEQ ID NO 24
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: 2-naphthyl alanine
<220> FEATURE:
<221> NAME/KEY: MOD_RES
<222> LOCATION: (4)..(4)
<223> OTHER INFORMATION: 2-naphthyl alanine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 24

Thr Xaa Glu Xaa Val Cys Ser Leu Met Cys Ser
1               5                   10

<210> SEQ ID NO 25
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker
```

<400> SEQUENCE: 25

Trp Trp Glu Trp Val Cys Ser Leu Met Cys Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 26

Trp Trp Glu Trp Trp Cys Ser Leu Met Cys Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 27

Phe Phe Glu Phe Phe Cys Ser Leu Met Cys Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys3 through an alpha,alpha'-
      xylylene linker

<400> SEQUENCE: 28

Thr Ser Cys Glu Val Met Ser Leu Met Cys Ser
1               5                   10

<210> SEQ ID NO 29
<211> LENGTH: 11
<212> TYPE: PRT

<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 29

Phe Phe Glu Phe Phe Cys Gln Leu Met Cys Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 30

Thr Ser Glu Glu Val Cys Ser Leu Phe Cys Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: 2-naphthyl alanine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 31

Trp Trp Xaa Trp Phe Cys Ser Phe Phe Cys Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: chemically synthesized

<400> SEQUENCE: 32

```
Ser Glu Glu Val Val Gln Lys Met Thr Gly Leu
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 33

```
Ser Cys Glu Val Val Cys Lys Met Thr Gly Leu
1               5                   10
```

<210> SEQ ID NO 34
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 34

```
Gln Cys Glu Val Val Cys Lys Met Thr Gly Leu
1               5                   10
```

<210> SEQ ID NO 35
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 35

```
Ser Cys Glu Leu Val Cys Lys Met Thr Gly Leu
1               5                   10
```

<210> SEQ ID NO 36
<211> LENGTH: 11
<212> TYPE: PRT
<213> ORGANISM: Artificial Sequence
<220> FEATURE:
<223> OTHER INFORMATION: chemically synthesized

```
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 36

Ser Cys Glu His Val Cys Lys Met Thr Gly Leu
1               5                   10

<210> SEQ ID NO 37
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 37

Ser Cys Glu Ser Val Cys Lys Met Thr Gly Leu
1               5                   10

<210> SEQ ID NO 38
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 38

Ser Cys Glu Val Val Cys Arg Met Thr Gly Leu
1               5                   10

<210> SEQ ID NO 39
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
```

```
<400> SEQUENCE: 39

Ser Cys Glu Val Val Cys Lys Pro Thr Gly Leu
1               5                   10

<210> SEQ ID NO 40
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 40

Ser Cys Glu Val Val Cys Lys Trp Thr Gly Leu
1               5                   10

<210> SEQ ID NO 41
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 41

Ser Cys Glu Val Val Cys Lys Met Trp Gly Leu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 42

Ser Cys Glu Val Val Cys Lys Met Phe Gly Leu
1               5                   10

<210> SEQ ID NO 43
<211> LENGTH: 11
<212> TYPE: PRT
```

```
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (10)..(10)
<223> OTHER INFORMATION: bAla

<400> SEQUENCE: 43

Ser Cys Glu Val Val Cys Lys Met Thr Xaa Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 44

Ser Cys Glu Val Val Cys Lys Met Thr Gly Pro
1               5                   10

<210> SEQ ID NO 45
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: 2-naphthyl alanine

<400> SEQUENCE: 45

Ser Cys Glu Val Val Cys Lys Met Trp Gly Xaa
1               5                   10

<210> SEQ ID NO 46
<211> LENGTH: 11
<212> TYPE: PRT
<213> ORGANISM: Artificial Sequence
<220> FEATURE:
```

<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 46

Ser Cys Glu Val Val Cys Lys Met Trp Gly Pro
1               5                   10

<210> SEQ ID NO 47
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 47

Ser Cys Glu Glu Val Cys Lys Pro Gly Gly Pro
1               5                   10

<210> SEQ ID NO 48
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 48

Asn Cys Glu Val Asn Cys Lys Gln Thr Gly Leu
1               5                   10

<210> SEQ ID NO 49
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'- xylylene linker
<220> FEATURE:
<221> NAME/KEY: MOD_RES
<222> LOCATION: (10)..(10)
<223> OTHER INFORMATION: bAla

<400> SEQUENCE: 49

Ser Cys Glu Thr Val Cys Lys Pro Thr Xaa Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 50

Ser Cys Glu Ser Val Cys Lys Pro Trp Gly Pro
1               5                   10

<210> SEQ ID NO 51
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (10)..(10)
<223> OTHER INFORMATION: bAla

<400> SEQUENCE: 51

Asn Cys Glu Thr Asn Cys Lys Pro Trp Xaa Pro
1               5                   10

<210> SEQ ID NO 52
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker -continued

```
<400> SEQUENCE: 52

Ser Cys Glu Val Val Cys Lys Phe Thr Gly Leu Lys Val Pro
1               5                   10

<210> SEQ ID NO 53
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 53

Ser Cys Glu Val Val Cys Lys Met Thr Gly Leu Lys Phe Pro
1               5                   10

<210> SEQ ID NO 54
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (14)..(14)
<223> OTHER INFORMATION: 2-naphthyl alanine

<400> SEQUENCE: 54

Ser Cys Glu Ser Val Cys Lys Met Thr Gly Leu Lys Val Xaa
1               5                   10

<210> SEQ ID NO 55
<211> LENGTH: 14
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 55

Ser Cys Glu Ser Val Cys Lys Pro Trp Gly Pro Lys Val Pro
1               5                   10
```

```
<210> SEQ ID NO 56
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 56

Ser Cys Glu Val Val Cys Lys Met Thr Gly Leu Lys Val Pro Leu
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 57

Ser Cys Glu Ser Val Cys Lys Trp Thr Gly Leu Lys Val Pro Leu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker

<400> SEQUENCE: 58

Ser Cys Glu Ser Val Cys Lys Met Trp Gly Leu Lys Val Pro Leu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
```

```
    xylylene linker
<220> FEATURE:
<221> NAME/KEY: MOD_RES
<222> LOCATION: (6)..(6)
<223> OTHER INFORMATION: connected to Cys2 through an alpha,alpha'-
    xylylene linker
<220> FEATURE:
<221> NAME/KEY: MOD_RES
<222> LOCATION: (11)..(11)
<223> OTHER INFORMATION: 2-naphthyl alanine
<220> FEATURE:
<221> NAME/KEY: misc_feature
<222> LOCATION: (15)..(15)
<223> OTHER INFORMATION: Xaa can be any naturally occurring amino acid

<400> SEQUENCE: 59

Ser Cys Glu Ser Val Cys Lys Met Thr Gly Leu Lys Val Pro Xaa
1               5                   10                  15

<210> SEQ ID NO 60
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (10)..(10)
<223> OTHER INFORMATION: bAla

<400> SEQUENCE: 60

Asn Cys Glu Thr Asn Cys Lys Pro Phe Xaa Pro
1               5                   10

<210> SEQ ID NO 61
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (4)..(4)
<223> OTHER INFORMATION: connected to Cys8 through an alpha,alpha'-
    xylylene linker
<220> FEATURE:
<221> NAME/KEY: MOD_RES
<222> LOCATION: (8)..(8)
<223> OTHER INFORMATION: connected to Cys4 through an alpha,alpha'-
    xylylene linker

<400> SEQUENCE: 61

Ser Glu Glu Cys Val Gln Lys Cys Thr Gly Leu
1               5                   10

<210> SEQ ID NO 62
<211> LENGTH: 10
<212> TYPE: PRT
<213> ORGANISM: Artificial Sequence
<220> FEATURE:
<223> OTHER INFORMATION: chemically synthesized

<400> SEQUENCE: 62
```

```
Ile Pro Pro Lys Tyr Arg Glu Leu Leu Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: connected to Cys7 through an alpha,alpha'-
      xylylene linker
<220> FEATURE:
<221> NAME/KEY: MOD_RES
<222> LOCATION: (7)..(7)
<223> OTHER INFORMATION: connected to Cys3 through an alpha,alpha'-
      xylylene linker

<400> SEQUENCE: 63

Ile Pro Cys Lys Tyr Arg Cys Leu Leu Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (4)..(4)
<223> OTHER INFORMATION: connected to Cys8 through an alpha,alpha'-
      xylylene linker
<220> FEATURE:
<221> NAME/KEY: MOD_RES
<222> LOCATION: (8)..(8)
<223> OTHER INFORMATION: connected to Cys4 through an alpha,alpha'-
      xylylene linker

<400> SEQUENCE: 64

Ile Pro Pro Cys Tyr Arg Glu Cys Leu Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 65

Ile Pro Pro Lys Tyr Cys Glu Leu Leu Cys
1               5                   10

<210> SEQ ID NO 66
<211> LENGTH: 11
<212> TYPE: PRT
<213> ORGANISM: Artificial Sequence
<220> FEATURE:
```

```
<223> OTHER INFORMATION: chemically synthesized
<220> FEATURE:
<221> NAME/KEY: MOD_RES
<222> LOCATION: (7)..(7)
<223> OTHER INFORMATION: connected to Cys11 through an alpha,alpha'-
      xylylene linker
<220> FEATURE:
<221> NAME/KEY: MOD_RES
<222> LOCATION: (11)..(11)
<223> OTHER INFORMATION: connected to Cys7 through an alpha,alpha'-
      xylylene linker

<400> SEQUENCE: 66

Ile Pro Pro Lys Tyr Arg Cys Leu Leu Ala Cys
1               5                   10

<210> SEQ ID NO 67
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (13)..(13)
<223> OTHER INFORMATION: connected to Cys17 through an alpha,alpha'-
      xylylene linker
<220> FEATURE:
<221> NAME/KEY: MOD_RES
<222> LOCATION: (17)..(17)
<223> OTHER INFORMATION: connected to Cys13 through an alpha,alpha'-
      xylylene linker

<400> SEQUENCE: 67

Leu Gly Lys Arg Glu Val Thr Ile Pro Pro Lys Tyr Cys Glu Leu Leu
1               5                   10                  15

Cys

<210> SEQ ID NO 68
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (13)..(13)
<223> OTHER INFORMATION: connected to Cys17 through an alpha,alpha'-
      xylylene linker
<220> FEATURE:
<221> NAME/KEY: MOD_RES
<222> LOCATION: (17)..(17)
<223> OTHER INFORMATION: connected to Cys13 through an alpha,alpha'-
      xylylene linker

<400> SEQUENCE: 68

Leu Phe Lys Arg Glu Val Thr Ile Pro Pro Lys Tyr Cys Glu Leu Leu
1               5                   10                  15

Cys

<210> SEQ ID NO 69
<211> LENGTH: 13
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (9)..(9)
<223> OTHER INFORMATION: connected to Cys13 through an alpha,alpha'-
      xylylene linker
```

```
<220> FEATURE:
<221> NAME/KEY: MOD_RES
<222> LOCATION: (13)..(13)
<223> OTHER INFORMATION: connected to Cys9 through an alpha,alpha'-
      xylylene linker

<400> SEQUENCE: 69

Glu Val Thr Ile Pro Pro Lys Tyr Cys Glu Leu Leu Cys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (8)..(8)
<223> OTHER INFORMATION: connected to Cys12 through an alpha,alpha'-
      xylylene linker
<220> FEATURE:
<221> NAME/KEY: MOD_RES
<222> LOCATION: (12)..(12)
<223> OTHER INFORMATION: connected to Cys8 through an alpha,alpha'-
      xylylene linker

<400> SEQUENCE: 70

Xaa Ala Ile Pro Pro Lys Tyr Cys Glu Leu Leu Cys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 71

Asp Pro Pro Lys Tyr Cys Glu Leu Leu Cys
1               5                   10

<210> SEQ ID NO 72
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker
```

<400> SEQUENCE: 72

Ala Pro Pro Lys Tyr Cys Glu Leu Leu Cys
1               5                   10

<210> SEQ ID NO 73
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 73

Pro Pro Pro Lys Tyr Cys Glu Leu Leu Cys
1               5                   10

<210> SEQ ID NO 74
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 74

Leu Pro Pro Lys Tyr Cys Glu Leu Leu Cys
1               5                   10

<210> SEQ ID NO 75
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: d-phenylalanine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 75

Xaa Pro Pro Lys Tyr Cys Glu Leu Leu Cys
1               5                   10

```
<210> SEQ ID NO 76
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 76

Gln Pro Pro Lys Tyr Cys Glu Leu Leu Cys
1               5                   10

<210> SEQ ID NO 77
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: pentafluorophenylalanine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 77

Ile Xaa Pro Lys Tyr Cys Glu Leu Leu Cys
1               5                   10

<210> SEQ ID NO 78
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 78

Ile Pro Pro Ala Tyr Cys Glu Leu Leu Cys
1               5                   10

<210> SEQ ID NO 79
<211> LENGTH: 10
<212> TYPE: PRT
<213> ORGANISM: Artificial Sequence
<220> FEATURE:
<223> OTHER INFORMATION: chemically synthesized
```

```
<220> FEATURE:
<221> NAME/KEY: MOD_RES
<222> LOCATION: (4)..(4)
<223> OTHER INFORMATION: N-epsilon-acetyllysine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 79

Ile Pro Pro Xaa Tyr Cys Glu Leu Leu Cys
1               5                   10

<210> SEQ ID NO 80
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 80

Ile Pro Pro Arg Tyr Cys Glu Leu Leu Cys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 81

Ile Pro Pro Lys Ala Cys Glu Leu Leu Cys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (5)..(5)
<223> OTHER INFORMATION: 4,4'-biphenylalanine
<220> FEATURE:
<221> NAME/KEY: MOD_RES
```

```
<222> LOCATION: (5)..(5)
<223> OTHER INFORMATION: 4,4'-biphenylalanine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 82

Ile Pro Pro Lys Xaa Cys Glu Leu Leu Cys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (5)..(5)
<223> OTHER INFORMATION: O-benzyltyrosine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 83

Ile Pro Pro Lys Xaa Cys Glu Leu Leu Cys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 84

Ile Pro Pro Lys Tyr Cys Ala Leu Leu Cys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
```

```
       xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 85

Ile Pro Pro Lys Tyr Cys Glu Gln Leu Cys
1               5                   10

<210> SEQ ID NO 86
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 86

Ile Pro Pro Lys Tyr Cys Glu Ala Leu Cys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (8)..(8)
<223> OTHER INFORMATION: Dbu
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 87

Ile Pro Pro Lys Tyr Cys Glu Xaa Leu Cys
1               5                   10

<210> SEQ ID NO 88
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker
```

```
<400> SEQUENCE: 88

Ile Pro Pro Lys Tyr Cys Glu Leu Phe Cys
1               5                   10

<210> SEQ ID NO 89
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (9)..(9)
<223> OTHER INFORMATION: phenylglycine
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 89

Ile Pro Pro Lys Tyr Cys Glu Leu Xaa Cys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 90

Ile Pro Pro Lys Tyr Cys Glu Leu Ala Cys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 91

Ile Pro Pro Arg Trp Cys Glu Leu Leu Cys
1               5                   10
```

```
<210> SEQ ID NO 92
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 92

Xaa Pro Pro Lys Tyr Cys Glu Leu Glu Cys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (2)..(2)
<223> OTHER INFORMATION: pentafluorophenylalanine
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 93

Ile Xaa Pro Arg Tyr Cys Glu Leu Leu Cys
1               5                   10

<210> SEQ ID NO 94
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (3)..(3)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys3 through an alpha,alpha'-
      xylylene linker

<400> SEQUENCE: 94

Ile Pro Cys Tyr Arg Cys Leu Leu Ala
1               5

<210> SEQ ID NO 95
```

```
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 95

Ile Pro Pro Arg Tyr Cys Glu Gln Leu Cys
1               5                   10

<210> SEQ ID NO 96
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 96

Xaa Pro Pro Lys Tyr Cys Glu Gln Leu Cys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 97

Ile Pro Pro Lys Trp Cys Glu Gln Leu Cys
1               5                   10

<210> SEQ ID NO 98
<211> LENGTH: 10
<212> TYPE: PRT
<213> ORGANISM: Artificial Sequence
<220> FEATURE:
<223> OTHER INFORMATION: chemically synthesized
<220> FEATURE:
```

```
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker

<400> SEQUENCE: 98

Ile Pro Pro Lys Tyr Cys Glu Leu Gln Cys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: N-ACETYLATION
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker
<220> FEATURE:
<221> NAME/KEY: MOD_RES
<222> LOCATION: (10)..(10)
<223> OTHER INFORMATION: AMIDATION

<400> SEQUENCE: 99

Ile Pro Pro Lys Tyr Cys Glu Leu Gln Cys
1               5                   10

<210> SEQ ID NO 100
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: N-ACETYLATION
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: AMIDATION

<400> SEQUENCE: 100

Ser Cys Glu Ser Val Cys Lys Pro Trp Gly Pro
1               5                   10

<210> SEQ ID NO 101
```

```
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: N-ACETYLATION
<220> FEATURE:
<221> NAME/KEY: MOD_RES
<222> LOCATION: (2)..(2)
<223> OTHER INFORMATION: connected to Cys6 through an alpha,alpha'-
      xylylene linker
<220> FEATURE:
<221> NAME/KEY: MOD_RES
<222> LOCATION: (4)..(4)
<223> OTHER INFORMATION: 4,4'-biphenylalanine
<220> FEATURE:
<221> NAME/KEY: MOD_RES
<222> LOCATION: (6)..(6)
<223> OTHER INFORMATION: connected to Cys2 through an alpha,alpha'-
      xylylene linker
<220> FEATURE:
<221> NAME/KEY: MOD_RES
<222> LOCATION: (11)..(11)
<223> OTHER INFORMATION: 2-naphthyl alanine
<220> FEATURE:
<221> NAME/KEY: MOD_RES
<222> LOCATION: (11)..(11)
<223> OTHER INFORMATION: AMIDATION

<400> SEQUENCE: 101

Ser Cys Glu Xaa Arg Cys Val Met Asn Gly Xaa
1               5                   10

<210> SEQ ID NO 102
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: N-ACETYLATION
<220> FEATURE:
<221> NAME/KEY: MOD_RES
<222> LOCATION: (6)..(6)
<223> OTHER INFORMATION: connected to Cys10 through an alpha,alpha'-
      xylylene linker
<220> FEATURE:
<221> NAME/KEY: MOD_RES
<222> LOCATION: (10)..(10)
<223> OTHER INFORMATION: connected to Cys6 through an alpha,alpha'-
      xylylene linker
<220> FEATURE:
<221> NAME/KEY: MOD_RES
<222> LOCATION: (11)..(11)
<223> OTHER INFORMATION: AMIDATION

<400> SEQUENCE: 102

Trp Trp Glu Trp Trp Cys Ser Leu Met Cys Ser
1               5                   10
```

ALPHA-HELICAL PEPTIDOMIMETIC INHIBITORS AND METHODS USING SAME

CROSS REFERENCE TO RELATED APPLICATIONS

This application is a U.S. national phase application filed under 35 U.S.C. §371 claiming priority to International Patent Application No. PCT/US13/38448, filed on Apr. 26, 2013, which claims priority to U.S. Provisional App. Ser. No. 61/639,552, filed Apr. 27, 2012 each of which are incorporated by reference herein in their entireties.

BACKGROUND OF THE INVENTION

Cysteine protease regulation has a wide range of potential therapeutic applications. For example, the papain family of cysteine proteases, which are widely distributed in diverse species including mammals, invertebrates, protozoa, plants and bacteria, are involved in normal cellular functions and have been implicated in a number of diseases, including cancer (Dumartin, et al., 2011, Cancer Res. 71:7091-7102), neurodegenerative diseases (Schechter & Ziv, 2011, Biol. Chem. 392:555-569), heart disease (Cheng, et al., 2011, Hypertension 58:978-986), viral infection (Bertram, et al., 2011, J. Virol. 85:13363-13372), ischemia/reperfusion injury (Shintani-Ishida & Yoshida, 2011, Biochim. Biophys. Acta 1812:743-751), osteoporosis (Stoch & Wagner, 2008, Clin. Pharmacol. Ther. 83:172-176), and parasite infection (Chandramohanadas et al., 2011, PLoS One 6:e20869).

Inhibitors of cysteine proteases are known. For example, vinyl sulfones, which irreversibly inhibit cysteine proteases such as the cathepsins B, L, S, O2 and cruzain, have been identified as cysteine protease inhibitors. Other classes of compounds, such as aldehydes, nitriles, α-ketocarbonyl compounds, halomethyl ketones, diazomethyl ketones, (acyloxy)methyl ketones, ketomethylsulfonium salts and epoxy succinyl compounds (Palmer, 1995, J. Med. Chem. 38, 3193) have also been reported as cysteine protease inhibitors. U.S. Pat. No. 4,518,528 discloses peptidyl fluoromethyl ketones as irreversible inhibitors of cysteine protease. International Patent Application Publication No. WO 94/04172, and European Patent Application Nos. EP 0 525 420 A1, EP 0 603 873 A1, and EP 0 611 756 A2 describe alkoxymethyl and mercaptomethyl ketones that inhibit the cysteine proteases cathepsins B, H and L. Azapeptides, which are designed to deliver the azaamino acid to the active site of serine proteases, are known to inhibit serine proteases (Elmore et al., 1968, Biochem. J. 107, 103, Garker et al., 1974, Biochem. J. 139, 555, Gray et al., 1977, Tetrahedron 33, 837, Gupton et al., 1984, J. Biol. Chem. 259, 4279, Powers et al., 1984, J. Biol. Chem. 259, 4288).

However, while a structurally diverse variety of protease inhibitors have been identified, these known inhibitors are not considered suitable for use as therapeutic agents in animals, especially humans, because they suffer from numerous shortcomings, including cytotoxicity, poor solubility, overly rapid plasma clearance, and particularly a lack of specificity.

There is a need in the art for novel specific protease inhibitors. Such inhibitors would be useful for treating diseases caused by pathological levels of proteases, particularly cysteine proteases. The present invention fulfills these needs.

BRIEF SUMMARY OF THE INVENTION

The invention includes a composition comprising a peptide, or a salt thereof, having at least one α-helix, wherein the peptide inhibits a protease.

In one embodiment, the peptide comprises at least two cysteine residues, wherein the at least two cysteine residues occupy i,i+4 positions in the peptide and are covalently connected through a linker. In another embodiment, the linker comprises alpha,alpha'-meta-xylylene. In yet another embodiment, the protease is a cysteine protease. In yet another embodiment, the cysteine protease comprises at least one selected from the group consisting of calpain, cathepsin K, cathepsin L, and cathepsin S.

In one embodiment, the cysteine protease comprises calpain and the peptide comprises at least one selected from the group consisting of SEQ ID NOs:63-99. In another embodiment, the cysteine protease comprises calpain and the peptide comprises SEQ ID NO:85 or SEQ ID NO:99.

In one embodiment, the cysteine protease comprises cathepsin K and the peptide comprises at least one selected from the group consisting of SEQ ID NOs:33-61 and 100. In another embodiment, the cysteine protease comprises cathepsin K and the peptide comprises SEQ ID NO:50 or SEQ ID NO:100.

In one embodiment, the cysteine protease comprises cathepsin L and the peptide comprises at least one selected from the group consisting of SEQ ID NOs:2-13 and 101. In another embodiment, the cysteine protease comprises cathepsin L and the peptide comprises SEQ ID NO:9 or SEQ ID NO:101.

In one embodiment, the cysteine protease comprises cathepsin S and the peptide comprises at least one selected from the group consisting of SEQ ID NOs:15-31 and 102. In another embodiment, the cysteine protease comprises cathepsin S and the peptide comprises SEQ ID NO:26 or SEQ ID NO:102.

In one embodiment, the peptide further comprises a covalent modifying group. In another embodiment, the covalent modifying group comprises a nitrile, alpha beta unsaturated ketone, vinyl sulfone, or acyloxymethyl ketone.

The invention also includes a method of treating or preventing a disease or condition in a subject in need thereof, wherein the disease or condition is associated with dysfunctional cysteine protease regulation, the method comprising administering to the subject a therapeutically effective amount of a pharmaceutical composition comprising a peptide selected from the group consisting of SEQ ID NOs:2-13, 15-31, 33-61, 63-102 or a salt thereof, whereby administration of the composition to the subject treats or prevents the disease or condition in the subject.

In one embodiment, the disease or condition comprises cancer, tumor metastasis, metachromatic leukodystrophy, muscular dystrophy, amytrophy, diseases of excessive bone or cartilage loss, metabolic bone disease, gingival disease, neurodegenerative disease, arthritis, heart disease, viral infection, ischemia/reperfusion injury, Paget's disease, hypercalcemia or parasite infection. In another embodiment, the parasite infection comprises *Pneumocystis carinii* infection, *Trypsanoma cruzi* infection, *Trypsanoma brucei* infection, *Crithidia fusiculata* infection, schistosomiasis or malaria. In yet another embodiment, the viral infection includes SARS.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIG. 2A depicts a list of parent and lead cysteine protease inhibitors and their $K_i$ values The bold 'C' represents the cysteine linked at the i,i+4 position. Legends: N/A=not applicable because the inhibitor did not inhibitor; NT=not tested/to be tested; Bip=Ala(4,4'-biphenyl); nap=Ala(2-naphthyl)). FIG. 2B is a schematic representation of linked helical peptidomimetics. α,α'-Dibromo-meta-xylene is the i,i+4 linker. FIG. 2C illustrates circular dichroism spectra of unlinked (middle) and linked (right) peptidomimetics (key at left) in 50 mM Tris-HCl buffer (pH 7.5) and 40% trifluoroethanol (TFE). α-Helical stabilization substantially increases helicity in solution.

FIG. 3, comprising FIG. 3A illustrates a model of an activity-based probe. FIG. 3B illustrates a screen of possible amino acid spacers that could be used in linker 1: NM-01=A,A, NM-02=βA,A. NM-03=A, βP. FIG. 3C illustrates a titration of the activity based probe against Calpain-1 and Calpain-2. DCG-04 is a non-specific positive control. As illustrated, the probe labeled only active enzyme. FIG. 3D illustrates a titration of the activity based probe against Cathepsin K, Cathepsin L, and Cathepsin S. As illustrated, the probe did not label these cysteine proteases. FIG. 3E illustrates the calpain inhibitor tested on parasite infected red blood cells. As illustrated, the inhibitor inhibited egress similarly to the endogenous inhibitor.

FIG. 4, comprising

DETAILED DESCRIPTION OF THE INVENTION

Figure 1:
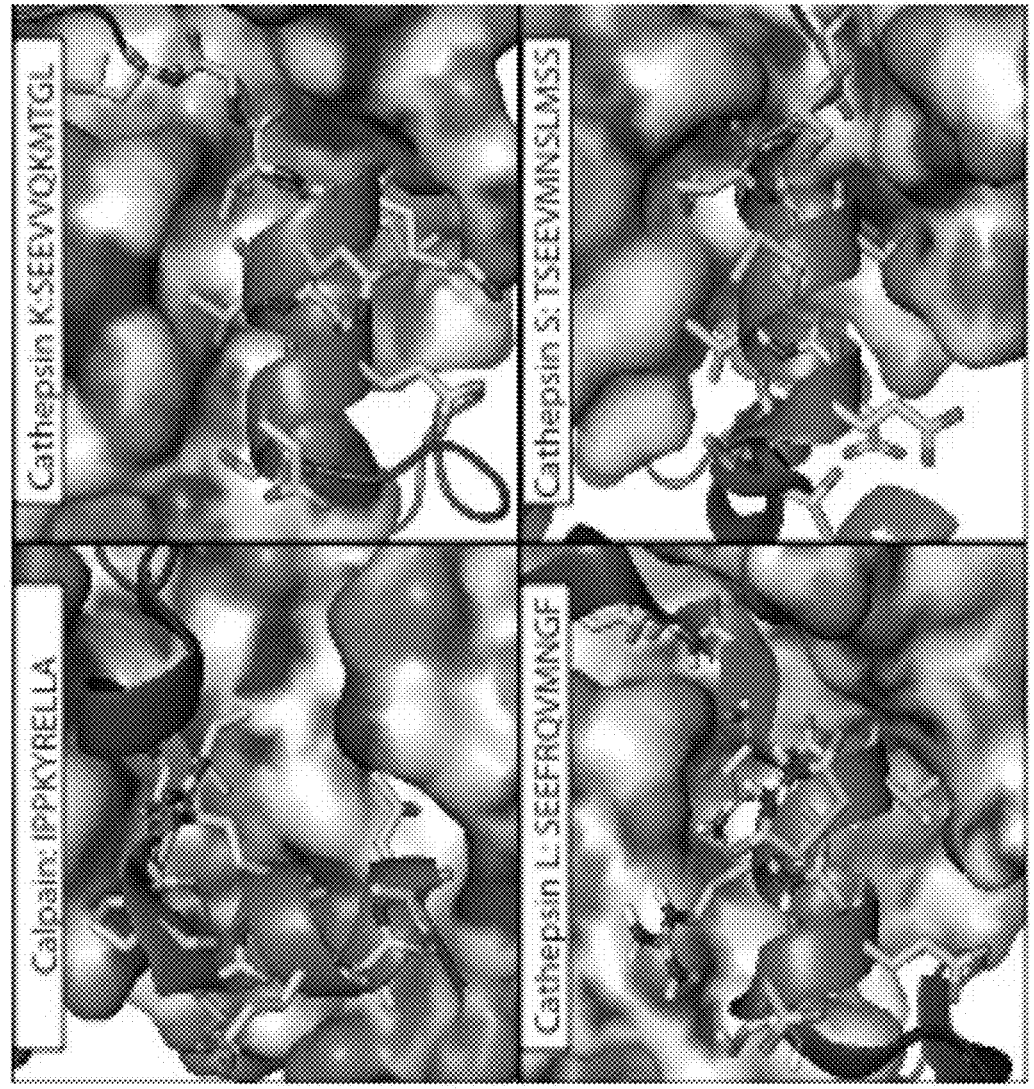
FIG. 1 is a series of drawings illustrating the inhibition of cysteine proteases by helical structures. The helical structures correspond to either the pro-domain or an endogenous inhibitor. The helices of papain family cysteine proteases Calpain, Cathespin K, L and S are illustrated. The peptide sequence is highlighted on the helix.

The present invention relates to a novel class of protease inhibitors with high protein binding affinity. In one embodiment, the present invention includes α-helical protease inhibitors that bind to and inhibit any class of proteases. In another embodiment, the present invention represents the first disclosure of a highly specific cysteine protease inhibitor. For example, the inhibitors of the present invention can differentiate between closely related proteases (such as, but not limited to, cathepsin L and cathepsin S), while displaying no binding affinity for other classes of proteases (including serine proteases, metalloproteases, threonine proteases, and aspartyl proteases).

In one embodiment, the inhibitors are α-helical peptidomimetics. In another embodiment, the inhibitors bind to and inhibit cysteine proteases with high specificity. In yet another embodiment, the inhibitors bind to and inhibit calpain or particular cathepsins, such as cathepsin K, L or S, with high specificity. In yet another embodiment, the inhibitors bind to and inhibit cathepsin L and cathepsin S with such distinct affinities that they can differentiate between cathepsin L and cathepsin S.

The inhibitors of the present invention may be used as therapeutic agent to treat a disease, whereby for example the inhibitors interrupt protein-protein interactions of proteases. Without wishing to be limited by theory, the inhibitors of the present invention may be used to treat infectious diseases such as SARS, neurological diseases such as Alzheimer's disease, conditions such as reperfusion injury, or cancer.

The present invention also includes an assay kit for identifying a protease in a sample. In one embodiment, the present invention includes an assay kit for identifying a protease, such as calpain, in cell lysates and live cell imaging. For example, the kit may include at least one cysteine protease probe and instructions for its use in the identification of protease activity, such as in a disease study, a cell life cycle study or other functional studies. In one embodiment, the probes of the present invention can be used to specifically label their respective activated proteases over unactivated proteins and other cysteine proteases.

DEFINITIONS

As used herein, each of the following terms has the meaning associated with it in this section. Unless defined otherwise, all technical and scientific terms used herein generally have the same meaning as commonly understood by one of ordinary skill in the art to which this invention belongs.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

As used herein, amino acids are represented by the full name thereof, by the three-letter code as well as the one-letter code corresponding thereto:

| Full Name | 3 Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the residue "C" (in bold font) in a peptide indicates that the cysteine residue is chemically modified with a bifunctional linker that covalently attaches this cysteine residue to another cysteine residue within the same peptide. In one embodiment, the linker comprises the alpha, alpha'-meta-xylylene linker:

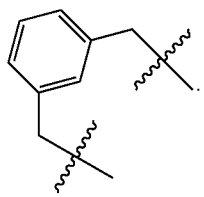 [SMILES: *Cc1cccc(C*)c1]

As used herein, the term "fragment," as applied to a protein or peptide, refers to a subsequence of a larger protein or peptide. A "fragment" of a protein or peptide may be at least about 10 amino acids in length; for example, at least about 50 amino acids in length; more preferably, at least about 100 amino acids in length; even more preferably, at least about 200 amino acids in length; particularly preferably, at least about 300 amino acids in length; and most preferably, at least about 400 amino acids in length.

As used herein, the term "homologous" refers to the subunit sequence similarity between two polymeric molecules, e.g., between two nucleic acid molecules, such as two DNA molecules or two RNA molecules, or between two protein molecules. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As used herein, "homology" is used synonymously with "identity."

As used herein, the term "substantially the same" amino acid sequence is defined as a sequence with at least 70%, preferably at least about 80%, more preferably at least about 85%, more preferably at least about 90%, even more preferably at least about 95%, and most preferably at least 99% homology with another amino acid sequence, as determined by the FASTA search method in accordance with Pearson & Lipman, 1988, Proc. Natl. Inst. Acad. Sci. USA 85:2444-48.

By the term "specifically bind" or "specifically binds," as used herein, is meant that a first molecule preferentially binds to a second molecule, but does not necessarily bind only to that second molecule.

"Isolated" means altered or removed from the natural state through the actions of a human being. For example, a nucleic acid or a protein naturally present in a living animal is not "isolated," but the same nucleic acid or protein partially or completely separated from the coexisting materials of its natural state is "isolated." An isolated nucleic acid or protein can exist in substantially purified form, or can exist in a non-native environment such as, for example, a host cell.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the terms "effective amount" and "pharmaceutically effective amount" refer to a nontoxic but sufficient amount of an agent or drug to provide the desired biological result. That result can be reduction and/or alleviation of the signs, symptoms, or causes of a disease or disorder, imaging or monitoring of an in vitro or in vivo system (including a living organism), or any other desired alteration of a biological system. An appropriate effective amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration. As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention includes non-covalent α-helical inhibitors of cysteine proteases, namely calpain, cathepsin L, cathepsin S and cathepsin K. In one embodiment, the inhibitors of the invention occupy mainly the prime side of the active site and do not interact with the active site cysteine.

In one embodiment, a warhead group is added to the C-terminus of the helical cathepsin inhibitors and to the N-terminus of the helical calpain inhibitors. This modification converts non-covalent inhibitors in covalent inhibitors. Distinct warhead groups such as nitriles, alpha beta unsaturated ketones, vinyl sulfones, and acyloxymethyl ketone may be used. In one embodiment, adding the warhead group increases the potency of these helical inhibitors.

Cathepsin L

The peptides SEEFRQVMNGF (SEQ ID NO:1), SECFRQCMNGF (SEQ ID NO:2), and SCEFRCVMNGF (SEQ ID NO:3) were synthesized based on visual inspection of co-crystal structure of the cathepsin L proenzyme. SEEFRQVMNGF had no inhibitory activity due to lack of helix stabilization. Without wishing to be limited by theory, the inhibitor SECFRQCMNGF may have low activity because its binding to the enzyme may have been disrupted by steric clashes of the linker with part of the enzyme, while in the case of inhibitor SCEFRCVMNGF, the linker is completely solvent exposed and unlikely to interact with the enzyme.

For cathepsin L, a hydrophobic pocket near the C-terminus as well as near the N-terminus was identified and may be exploited for optimizing potency of peptidic inhibitors. In the parent sequence phenylalanine is present in both of these hydrophobic pockets making π-π interactions with hydrophobic amino acid residues from the enzyme. Replacement of this residue with a non-natural amino acid residue equipped with a larger hydrophobic R-group may create a stronger hydrophobic interaction. Non-natural amino acids 2-napthylalanine and biphenylalanine were used to create inhibitors SCE(nap)RCVMNGF (SEQ ID NO:4), SCE(bip) RCVMNGF (SEQ ID NO:5), SCEFRCVMNG(nap) (SEQ ID NO:7), and SCE(bip)RCVMNG(nap) (SEQ ID NO:9). Biphenyalanine was not considered a viable option for the C-terminal residue due to perceived possible steric clashes with the enzyme, and/or possible loss of potency due to extension into the unprimed side of the enzyme. The use of these amino acids resulted in more potent inhibitors. In one embodiment, these inhibitors have increased binding selectivity because their binding to other enzymes is prevented due to the modified enzyme surface contours and subsequently increase steric hindrance.

(C-terminal stabilization location TSEEVCSLMCS) increased inhibition. At the N-terminal, two residues of the parent sequence appear to be part of a turn rather than the helix. Without wishing to be limited by theory, stabilization of TCEEVCSLMSS may change the orientation of these residues, resulting in unfavorable interactions between the linker or the side chains of the amino acids and the enzyme.

TSEEVCSLMCS was a much more potent inhibitor of cathepsin L over cathepsin S, and did not inhibit cathepsin K. Cathepsin L activity may be attributed to the similarity in charge and polarity of the amino acid residues at the N-terminus of the prodomains of cathepsin L and cathepsin S. The N-terminal residues of cathepsin S appear to have minimal interaction with the enzyme; the prodomain helix appears to bind to the active site at an angle. The enzyme area in proximity to the polar N-terminus of the prodomain is a large hydrophobic surface. In one embodiment, hydrophobic residues are introduced into the N-terminus of the cathepsin S inhibitor to increase binding and specificity, as cathepsin L and Cathepsin K have a much smaller and more localized hydrophobic surface.

Four of the five N-terminal residues were substituted with tryptophan beginning with single mutants, WSEEVCSLMCS (SEQ ID NO:17), TWEEVCSLMCS (SEQ ID NO:18), TSEWVCSLMCS (SEQ ID NO:20), and TSEEW-

TABLE 1

Biological data for cathepsin L inhibitors. nap=2-napthyl alanine; bip=4,4'-biphenylalanine. The linker used was alpha,alpha'-meta-xylylene, where applicable.

| SEQ ID NO: | | Calpain $K_i$ (μM) | Cathepsin L $K_i$ (μM) | Cathepsin S $K_i$ (μM) | Cathepsin K $K_i$ (μM) |
|---|---|---|---|---|---|
| 1 | SEEFRQVMNGF | N/A | >100 | N/A | N/A |
| 2 | SECFRQCMNGF | N/A | 84.7 ± 1.2 | N/A | N/A |
| 3 | SCEFRCVMNGF | >100 | 29.4 ± 1.1 | >100 | >100 increases activity at middle concentrations |
| 4 | SCE(nap)RCVMNGF | >100 | 6.06 ± 1.03 | 20.2 ± 1.05 | >100 |
| 5 | SCE(bip)RCVMNGF | >100 | 3.39 ± 1.03 | 43.1 ± 1.97 | >100 |
| 6 | SCEFRCVQNGF | | | | |
| 7 | SCEFRCVMNG(nap) | >100 | 6.70 ± 1.04 | 48.07 ± 1.21 | 64.28 ± 12.5 |
| 8 | SCEFACVMNGF | | | | |
| 9 | SCE(bip)RCVMNG(nap) | 19.8 ± 6.3 | 0.543 ± 1.2 | 27.4 ± 1.4 | 32.0 ± 1.17 |
| 10 | SCE(bip)RCVQNG(nap) | | | | |
| 11 | SCE(bip)RCVMN(d-R)(nap) | | | | |
| 12 | RCE(bip)QCVQNG(nap) | | 2.75 ± 1.05 | | |
| 13 | SCE(bip)RCVQN(d-R)(nap) | | | | |

Cathepsin S

TSEEVMNSLMSS (SEQ ID NO:14) was designed by isolating the sequence of the prodomain helix sitting at the active site and determining the parent sequence. TSEEVMNSLMSS did not demonstrate any intrinsic inhibitory activity because of the large energy barrier for helix formation. The helix was stabilized at two locations, TCEEVCSLMSS (SEQ ID NO:15) and TSEEVCSLMCS (SEQ ID NO:16). Only one of the stabilized α-helices CSLMCS (SEQ ID NO:21). Residue 3, glutamate, was not substituted because this residue appears to be involved in hydrogen bonding interactions with the enzyme via water molecules. Tryptophan was selected rather than phenylalanine based on its larger size. Single mutant studies indicated that changing any of the N-terminal residues to tryptophan substantially reduced the affinity of the peptides for cathepsin L. These single mutants were more potent and specific inhibitors of cathepsin S than the stabilized parent sequence.

Without wishing to be limited by theory, these results support the suggestion that incorporating large hydrophobic residues would hinder the binding of the inhibitor to the cathepsin L.

Mutating polar residues for hydrophobic residues at the N-terminus of the cathepsin S inhibitor increased selectivity, especially against cathepsin L. Double, triple and quadruple mutants of the cathepsin S inhibitor, TWEWVCSLMCS (SEQ ID NO:23), WWEWVCSLMCS (SEQ ID NO:25) and WWEWWCSLMCS (SEQ ID NO:26), were prepared. Double mutations resulted in a decrease in $K_i$ and specificity retention, i.e., the inhibitor was twice as specific for cathepsin S over cathepsin L. While the first amino acid mutation in the single mutant appeared to have no effect, when this mutation was combined with other mutations to form a triple mutant, it actually enhanced inhibitory activity resulting in a better inhibitor. The addition of this first amino acid mutation caused the inhibitor to become more specific for cathepsin S over cathepsin L and calpain. Without wishing to be limited by theory, adding both N-terminal hydrophobic residues may increase the helicity and subsequently the activity. The hydrophobic residues could provide greater helicity and/or slightly change the orientation of how the peptide binds to the enzyme, thereby eliminating the steric hindrance previously seen in the stabilized parent peptide and single mutant.

location was selected for stabilization: SCEVVCKMTGL (SEQ ID NO:33). The other i,i+4 stabilization considered, SECVVQCMTGL, was ruled out because in pymol the lysine appeared to be hydrogen bonded to a glutamine on the cathepsin K. Disrupting this bond could hamper the binding of the inhibitor.

This inhibitor worked differently than the previous inhibitors. Activity was reduced by 20% at the lowest and highest concentrations. At all other concentrations activity was actually enhanced, i.e., the peptide activated the enzyme rather than inhibiting it. Without wishing to be limited by theory, this activation was due to binding to an allosteric site. Cathepsin K is known to bind collagen fibers, and possibly the helix binds to a similar spot thereby stabilizing the peptide in an open conformation. This activation did not appear to be sequence specific as most of the inhibitors for cathepsin L and cathepsin S also activate cathepsin K. Interestingly, inhibitors containing large aromatic rings, such as tryptophan or biphenyl, appeared to reduce activation of cathepsin K.

Based on the cathepsin K substrate, a proline was placed at either the eighth residue from the N-terminus or at the last residue. In one embodiment, the inhibitor, if oriented correctly, aligns in the active site in the opposite orientation (C-terminus on the unprimed side for the inhibitor versus N-terminus on the unprimed side for substrates) preventing

TABLE 2

Biological data for cathepsin S inhibitors. nap=2-napthyl alanine; bip=4,4'-biphenylalanine. The linker used was alpha,alpha'-meta-xylylene, where applicable.

| SEQ ID NO: | Inhibitor | Cathepsin K $K_i$ (μM) | Cathepsin L $K_i$ (μM) | Cathepsin S $K_i$ (μM) | Calpain $K_i$ (μM) |
|---|---|---|---|---|---|
| 14 | TSEEVMNSLMSS | — | — | >100 | — |
| 15 | TCEEVCSLMSS | — | — | >100 | — |
| 16 | TSEEVCSLMCS | >100 | 16.72 ± 2.6 | 52.14 ± 1.05 | >100 |
| 17 | WSEEVCSLMCS | >100 | 75.98 ± 1.17 | 51.03 ± 1.22 | 108 ± 1.28 |
| 18 | TWEEVCSLMCS | 67.54 ± 1.15 | 93.85 ± 1.33 | 29.68 ± 1.08 | >100 |
| 19 | TSAEVCSLMCS | | | | |
| 20 | TSEWVCSLMCS | >100 | 57.05 ± 1.24 | 33.14 ± 1.07 | >100 |
| 21 | TSEEWCSLMCS | >100 | 104.7 ± 1.17 | 80.39 ± 1.15 | >100 |
| 22 | TSEEVCSFMCS | N/A | N/A | >100 | N/A |
| 23 | TWEWVCSLMCS | 65.74 ± 1.45 | 33.81 ± 1.16 | 14.3 ± 1.12 | 88.43 ± 1.13 |
| 24 | T(nap)E(nap)VCSLMCS | | | 12.86 ± 1.12 | |
| 25 | WWEWVCSLMCS | 19.52 ± 1.16 | 16.09 ± 1.41 | 6.74 ± 1.06 | 85.45 ± 1.30 |
| 26 | WWEWWCSLMCS | 37.90 ± 1.41 | 28.13 ± 1.11 | 1.23 ± 1.16 | 66.72 ± 1.24 |
| 27 | FFEFFCSLMCS | | | 13.14 ± 1.13 | |
| 28 | TSCEVMSLMCS | | | | |
| 29 | FFEFFCQLMCS | | | | |
| 30 | TSEEVCSLFCS | | | | |
| 31 | WW(bip)WFCSFFCS | | | | |

Cathepsin K

The unstabilized parent sequence, SEEVVQKMTGL (SEQ ID NO:32), did not inhibit cathepsin K. Only one cleavage of the amide bond. The proline at the eighth position may break the helix, creating a curve to force the rest of the peptide into the active site. The proline at the C-terminus may fill what appears to be a hydrophobic pocket on the unprimed side of the enzyme. Placing the proline at the eighth residue still resulted in activation of cathepsin K. However, similarly to the stabilized parent sequence, at higher concentrations inhibition of the enzyme was observed. Mutating the last residue of the inhibitor resulted in activation at higher concentrations, but inhibition at the lowest concentrations (0.5 μM-1 μM). At these lower concentrations there was a decrease in activity by 50%, but there was no complete inhibition. An inhibitor containing the substrate sequence, PGGP, at the C-terminus was also tested. This peptide did not inhibit cathepsin K but rather was cleaved by the enzyme.

Based on the examination of the procathepsin K crystal structure and results from the other assays, the threonine to tryptophan was mutated. The tryptophan may bind to a hydrophobic pocket on the enzyme, and subsequently lock the inhibitor into a specific orientation at the active site. With this mutation there was no substantial inhibition or activation of the cathepsin K.

The fourth residue, valine, was also mutated to serine with the intention of creating an electrostatic interaction with a glutamine on the enzyme surface. Similarly to the original stabilized helix, activation of cathepsin K was observed, followed by slight inhibition at higher concentrations. Without wishing to be limited by theory, these results suggest that this mutation did not create the desired interaction.

Based on these assay results, all mutations were combined to determine if presence of each mutation would result in a more satisfactory inhibitor. Without wishing to be limited by theory, the tryptophan may lock the inhibitor in place near the active site either by binding to the pocket at the active site or the hydrophobic space located just a little farther from the active site. In one embodiment, other inhibitors containing tryptophan, i.e., cathepsin S inhibitors, may have a similar effect on cathepsin K. In another embodiment, incorporating the tryptophan renders other mutations more potent. The quadruple mutant displayed normal kinetics as well as a lower $K_i$. In addition to the inhibitory activity, the inhibitor was completely specific for cathepsin K (up to 100 μM).

TABLE 3

Biological data for cathepsin K inhibitors. nap = 2-napthyl alanine; bip = 4,4'-biphenylalanine; b-Ala = beta-alanine. The linker used was alpha,alpha'-meta-xylylene, where applicable.

| SEQ ID NO: | | Calpain $K_i$ (μM) | Cathepsin L $K_i$ (μM) | Cathepsin S $K_i$ (μM) | Cathepsin K $K_i$ (μM) |
|---|---|---|---|---|---|
| 32 | SEEVVQKMTGL | N/A | N/A | N/A | >100 |
| 33 | SCEVVCKMTGL | >100 | >100 | >100 | 80% activity between 200-500 nM & 50 μM |
| 34 | QCEVVCKMTGL | | 46.2 ± 2.5 | 43.5 ± 1.1 | 76.83 ± 2.7 |
| 35 | SCELVCKMTGL | | | | 80% activity between 200-500 nM & 50 μM |
| 36 | SCELVCKMTGL | | | | >100 |
| 37 | SCESVCKMTGL | >100 (inhibition increase at 100 uM) | >100 | 10.8 ± 1.0 | >100 |
| 38 | SCEVVCRMTGL | | | | |
| 39 | SCEVVCKPTGL | >100 | 48.0 ± 1.2 | 58.3 ± 1.2 | >100 |
| 40 | SCEVVCKWTGL | | | | |
| 41 | SCEVVCKMWGL | | | | >100 |
| 42 | SCEVVCKMFGL | | | | |
| 43 | SCEVVCKMT(b-Ala)L | | | | >100 |
| 44 | SCEVVCKMTGP | | | 27.8 ± 1.5 | 1.343 ± 1.6-0.6588 ± 1.4 |
| 45 | SCEVVCKMWG(nap) | | | | 34.6 |
| 46 | SCEVVCKMWGP | | | | |
| 47 | SCEEVCKPGGP | | | | >100 |
| 48 | NCEVNCKQTGL | | | | |
| 49 | SCETVCKPT(b-Ala)L | | | | |
| 50 | SCESVCKPWGP | >100 | >100 | >100 | 17.22 ± 1.34 |

TABLE 3-continued

Biological data for cathepsin K inhibitors. nap = 2-napthyl alanine; bip = 4,4'-biphenylalanine; b-Ala = beta-alanine. The linker used was alpha,alpha'-meta-xylylene, where applicable.

| SEQ ID NO: | | Calpain $K_i$ (µM) | Cathepsin L $K_i$ (µM) | Cathepsin S $K_i$ (µM) | Cathepsin K $K_i$ (µM) |
|---|---|---|---|---|---|
| 51 | NCETNCKPW(b-Ala)P | | | | |
| 14-mers | | | | | |
| 52 | SCEVVCKFTGLKVP | | | | >100 |
| 53 | SCEVVCKMTGLKFP | | | | >100 |
| 54 | SCESVCKMTGLKV(nap) | | | | |
| 55 | SCESVCKPWGPKVP | | | | 16.25 ± 1.2 |
| 15-mer | | | | | |
| 56 | SCEVVCKMTGLKVPL | | | | 22.67 ± 1.98 |
| 57 | SCESVCKWTGLKVPL | | | | |
| 58 | SCESVCKMWGLKVPL | | | | |
| 59 | SCESVCKMTGLKVP(nap) | | | | |
| 60 | NCETNCKPF(Ala)P | | | | |
| 61 | SEECVQKCTGL | | | | |

Calpain

Two key mutations were introduced in the short calpain inhibitor. These mutations were a substitution of the proline near the N-terminus with a pentafluorophenylalalnine (pf5) to create a better π-π stacking and ring stacking with a calpain residue, and the substitution of lysine with arginine to create more electrostatic interactions. Both mutations resulted in better potency and selectivity.

The length of the inhibitor was also expanded to 17 amino acids. This lengthening allowed it to span across the active site adding more contacts for tighter binding and easier formation of the helix. Lengthening the inhibitor substantially increased potency and specificity.

TABLE 4

Biological data for calpain inhibitors. pf5=pentafluorophenylalanine; dab=diaminobutyric acid; Cit=citrulline; $^d$F=d-amino acid phenylalanine; K-Ac=lysine with an acetylated ε-amino group; OBn-Y=O-benzyltyrosine; Cit=citrulline. The linker used was alpha,alpha'-meta-xylylene, where applicable.

| SEQ ID NO: | Inhibitor | Calpain $K_i$ (µM) | Cathepsin L $K_i$ (µM) | Cathepsin S $K_i$ (µM) | Cathepsin K $K_i$ (µM) |
|---|---|---|---|---|---|
| 62 | IPPKYRELLA | >100 | N/A | N/A | N/A |
| 63 | IPCKYRCLLA | >100 | N/A | N/A | N/A |
| 64 | IPPCYRECLA | 95.57 ± 25.5 | N/A | N/A | N/A |
| 65 | IPPKYCELLC | 10.2 ± 2.9 | 39.9 ± 1.09 | 50.2 ± 1.18 | >100 |
| 66 | IPPKYRCLLAC | 7.5 ± 2.7 | 5.1 ± 1.1 | | |
| 67 | LGKREVTIPPKYCELLC | 3.6 ± 1.7 | >100 | 31.5 ± 1.1 | >100 |
| 68 | LFKREVTIPPKYCELLC | 1.3 ± 1.3 | 10.7 ± 1.1 | 41.5 ± 4.5 | >100 |
| 69 | EVTIPPKYCELLC | 5.3 ± 1.9 | 69.6 ± 1.5 | 31.3 ± 1.15 | >100 |
| 70 | (b-Ala)AIPPKYCELLC | 10.7 ± 3.5 | 42.0 ± 1.3 | 38.4 ± 1.1 | >100 |
| 71 | DPPKYCELLC | 27.63 ± 8.2 | N/A | N/A | N/A |
| 72 | APPKYCELLC | 65.6 ± 20.5 | 12.53 ± 1.2 | 26.1 ± 1.3 | |
| 73 | PPPKYCELLC | 45.31 ± 1.24 | N/A | N/A | N/A |

TABLE 4-continued

Biological data for calpain inhibitors. pf5=pentafluorophenylalanine; dab=diaminobutyric acid; Cit=citrulline; $^d$F=d-amino acid phenylalanine; K-Ac=lysine with an acetylated ε-amino group; OBn-Y=O-benzyltyrosine; Cit=citrulline. The linker used was alpha,alpha'-meta-xylylene, where applicable.

| SEQ ID NO: | Inhibitor | Calpain $K_i$ (µM) | Cathepsin L $K_i$ (µM) | Cathepsin S $K_i$ (µM) | Cathepsin K $K_i$ (µM) |
|---|---|---|---|---|---|
| 74 | LPPKYCELLC | 10.96 ± 3.6 | 38.1 ± 1.2 | 46.3 ± 1.2 | >100 |
| 75 | $^d$FPPKYCELLC | | | | |
| 76 | QPPKYCELLC | 35.02 ± 10.4 | | | |
| 77 | I(pf5)PKYCELLC | 5.09 ± 1.9 | 22.2 ± 1.11 | >100 | >100 |
| 78 | IPPAYCELLC | 17.7 ± 5.6 | 24.56 ± 1.2 | 20.74 ± 1.2 | >100 |
| 79 | IPP(K-Ac)YCELLC | | | | |
| 80 | IPPRYCELLC | 5.3 ± 2.0 | 37.9 ± 1.11 | 35.9 ± 1.06 | >100 |
| 81 | IPPKACELLC | >100 | 8.12 ± 1.2 | 16.8 ± 1.1 | |
| 82 | IPPK(bip)CELLC | 9.65 ± 3.2 | 1.9 ± 1.1 | 1.4 ± 1.1 | |
| 83 | IPPK(OBn-Y)CELLC | 21.26 ± 6.7 | 16.7 ± 1.3 | 3.3 ± 1.2 | |
| 84 | IPPKYCALLC | 28.9 ± 9.1 | 12.5 ± 1.1 | 15.6 ± 1.6 | |
| 85 | IPPKYCEQLC | 11.01 ± 3.6 | 66.23 ± 1.07 | 21.45 ± 1.06 | >100 |
| 86 | IPPKYCEALC | 30.9 ± 9.2 | 21.4 ± 1.2 | 13.9 ± 1.04 | |
| 87 | IPPKYCE(dab)LC | | | | |
| 88 | IPPKYCELFC | 27.86 ± 1.14 | | | |
| 89 | IPPKYCEL(phenylglycine)C | | | | |
| 90 | IPPKYCELAC | | | | |
| 91 | IPPRWCELLC | | 8.8 ± 1.2 | | |
| 92 | (Cit)PPKYCELEC | | | | |
| 93 | I(pf5)PRYCELLC | | | | |
| 94 | IPCYRCLLA | | | | |
| 95 | IPPRYCEQLC | | | | |
| 96 | (Cit)PPKYCEQLC | | | | |
| 97 | IPPKWCEQLC | | | | |

Compositions of the Invention

The present invention includes a protease inhibitor. In one embodiment, the inhibitor is an α-helical peptidomimetic. As contemplated herein, the inhibitors of the present invention include any peptide having an α-helix that inhibits a protease, reduces the activity of a protease, or interferes with the binding of a protease to another protein or small molecule.

In one embodiment, the inhibitor is a peptide with underivatized N-terminus and underivatized C-terminus. In another embodiment, the inhibitor is a peptide with underivatized N-terminus and an amidated C-terminus (i.e., the C-terminus is derivatized as the corresponding amide). In yet another embodiment, the inhibitor is a peptide with an acylated N-terminus (i.e., the amino group of the N-terminus is derivatized with an acyl group, i.e., acylated) and an underivatized C-terminus. In yet another embodiment, the inhibitor is a peptide with an acylated N-terminus and an amidated C-terminus. In yet another embodiment, the acyl group is the acetyl group.

In one embodiment, the peptide comprises at least two residues, wherein the at least two residues occupy i,i+4 positions in the peptide and are covalently connected through a linker. In another embodiment, each of the at least two residues is a cysteine reside. In yet another embodiment, the linker comprises alpha,alpha'-meta-xylylene.

In one embodiment, the inhibitor selectively inhibits a cysteine protease. In another embodiment, the inhibitor selectively inhibits a cathepsin. In yet another embodiment, the inhibitor selectively inhibits cathepsin K, L or S. In yet another embodiment, the inhibitor selectively inhibits calpain. In yet another embodiment, the inhibitors of the present invention can differentiate between closely related proteases (i.e., binds to and inhibits one proteases in detriment of another, such as but not limited to cathepsin L and cathepsin S) and have no activity against other classes of proteases (including serine proteases, metalloproteases, threonine proteases, and aspartyl proteases).

In one embodiment, the inhibitor is a calpain inhibitor, wherein the inhibitor comprises compound (Ia) (IPP-KYCEQLC; SEQ ID NO:85), compound (Ib) (Ac-IPP-KYCEQLC-NH$_2$; SEQ ID NO: 99) or a salt thereof:

NO:98). In yet another embodiment, the inhibitor has at least 85% homology to compound (Ia) or (Ib). In yet another embodiment, the calpain inhibitor is a peptide selected from the group consisting of SEQ ID NOs:63-99.

In one embodiment, the inhibitor is a cathepsin K inhibitor, wherein the inhibitor comprises compound (IIa) (SCES-

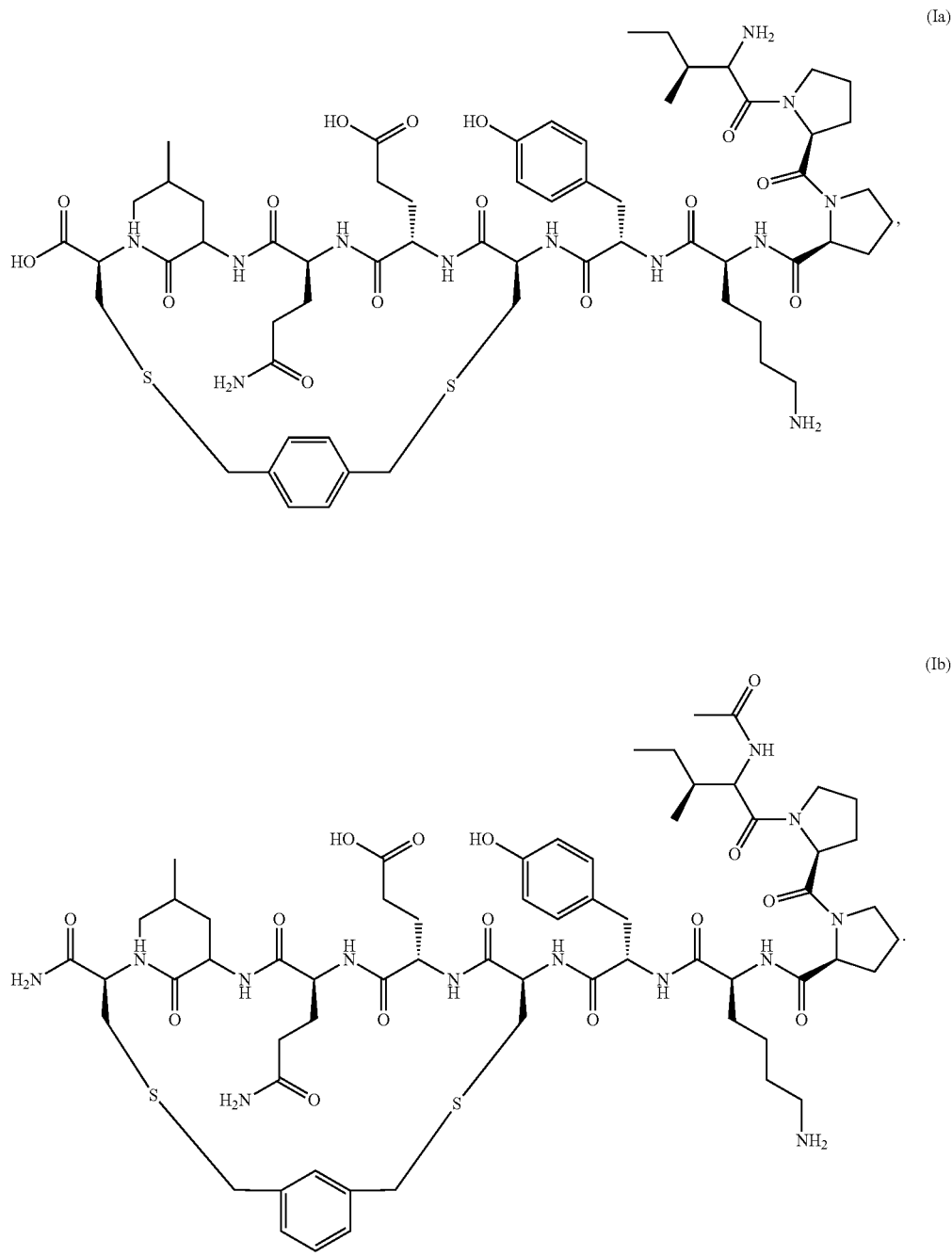

In another embodiment, the inhibitor is a calpain inhibitor peptide comprising the sequence IPPKYCELQC (SEQ ID VCKPWGP; SEQ ID NO:50), (IIb) (Ac-SCESVCKPWGP-NH$_2$; SEQ ID NO:100), or a salt thereof:

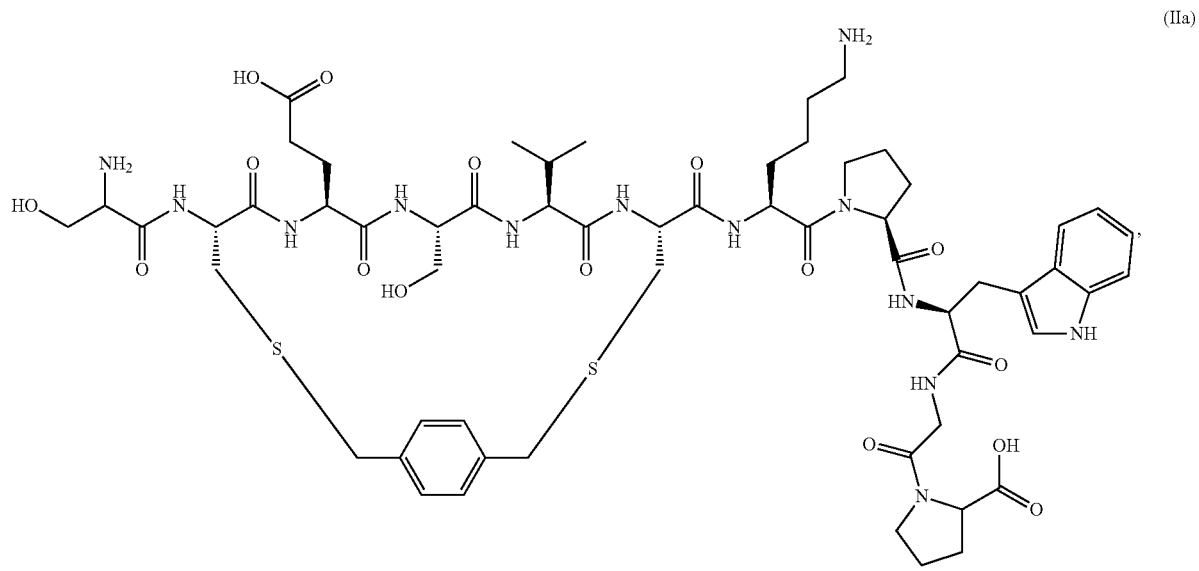

(IIa)

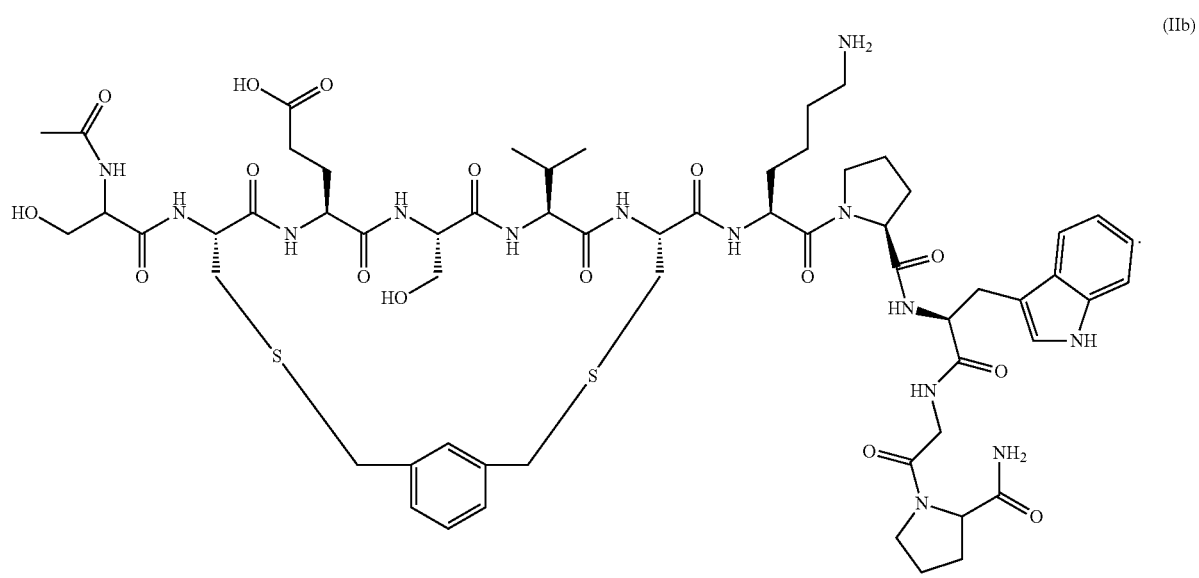

(IIb)

In another embodiment, the inhibitor is a cathepsin K inhibitor peptide comprising the sequence SCESVCKP-WGP (SEQ ID NO:50). In yet another embodiment, the inhibitor has at least 85% homology to compound (IIa) or (IIb). In yet another embodiment, the calpain inhibitor is a peptide selected from the group consisting of SEQ ID NOs:33-61 and 100.

In one embodiment, the inhibitor is a cathepsin L inhibitor, wherein the inhibitor comprises compound (IIIa) (SCE(bip)RCVMNG(nap); SEQ ID NO:9), compound (IIIb) (Ac-SCE(bip)RCVMNG(nap); SEQ ID NO:101) or a salt thereof:

(IIIa)

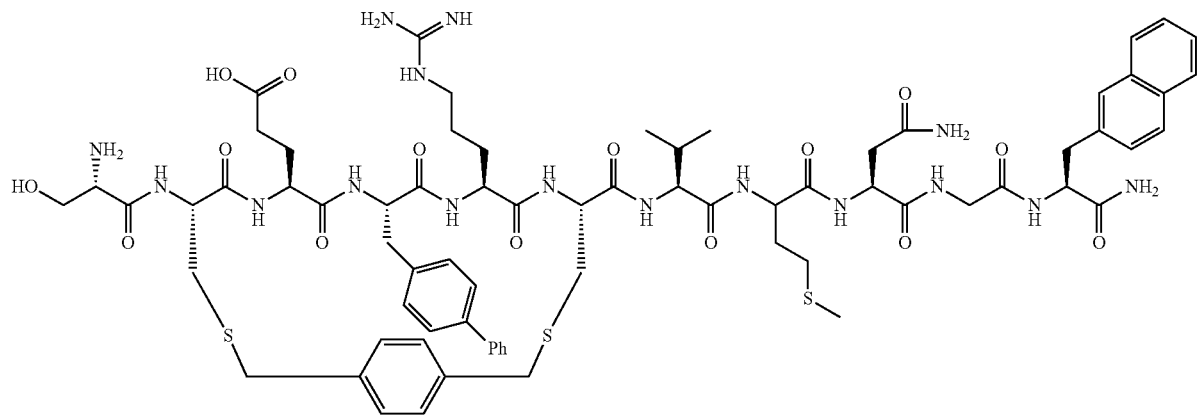

(IIIb)

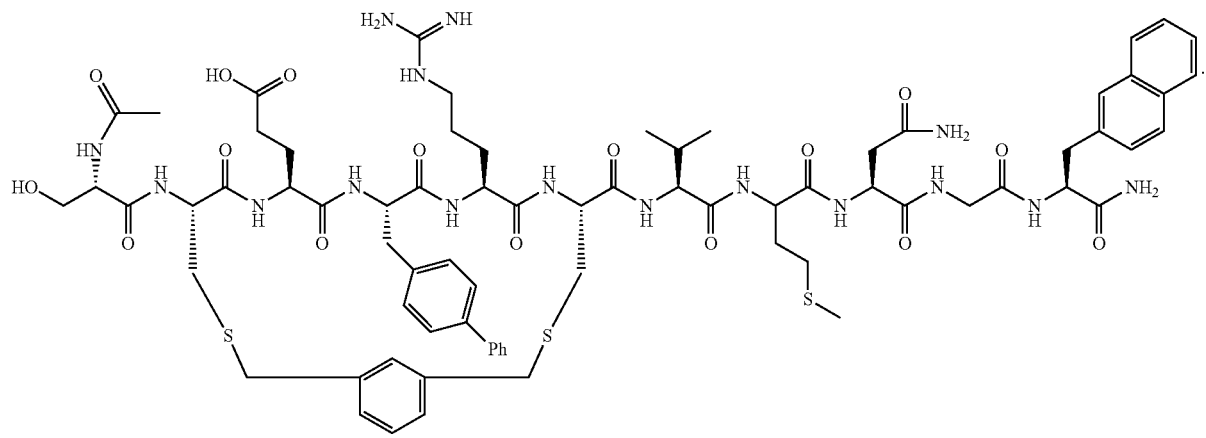

In another embodiment, the inhibitor is a cathepsin L inhibitor peptide comprising the sequence SCE(bip)RCVMNG(nap) (SEQ ID NO:9). In yet another embodiment, the inhibitor has at least 85% homology to compound (IIIa) or (IIIb). In yet another embodiment, the calpain inhibitor is a peptide selected from the group consisting of SEQ ID NOs:2-13 and 101.

In one embodiment, the inhibitor is a cathepsin S inhibitor, wherein the inhibitor comprises compound (IVa) (WWEWWCSLMCS; SEQ ID NO:26), compound (IVb) (Ac-WWEWWCSLMCS-NH₂; SEQ ID NO:102) or a salt thereof:

(IVa)

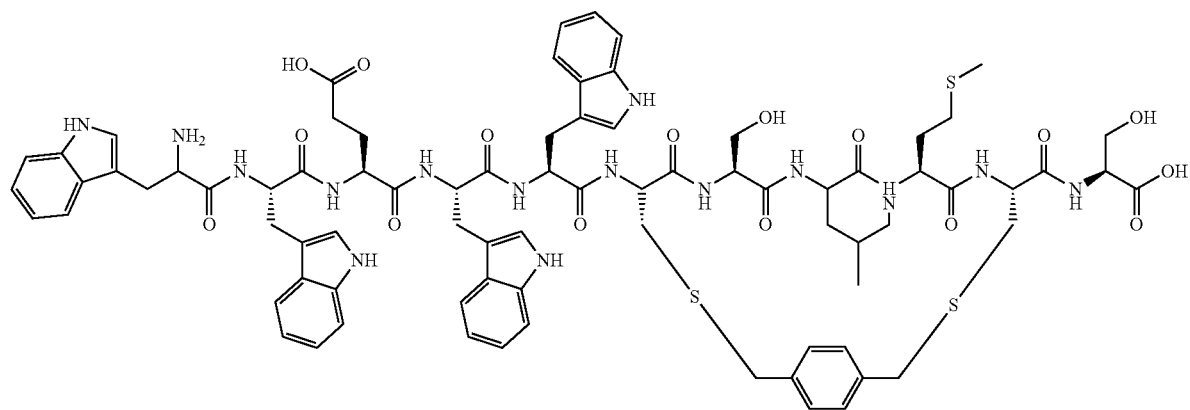

(IVb)

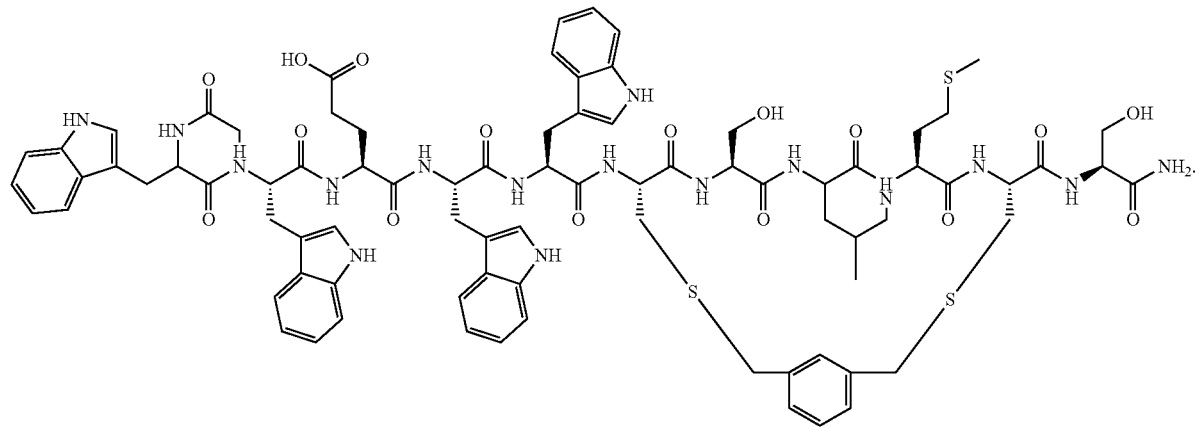

In another embodiment, the inhibitor is a cathepsin S inhibitor peptide comprising the sequence WWEWWCSLMCS (SEQ ID NO:26). In yet another embodiment, the inhibitor has at least 85% homology to compound (IVa) or (IVb). In yet another embodiment, the calpain inhibitor is a peptide selected from the group consisting of SEQ ID NOs:15-31 and 102.

In one embodiment, the invention includes a composition comprising a peptide-containing moiety, wherein the peptide-containing moiety comprises a sequence selected from SEQ ID NOs:2-13, 15-31, 33-61, 63-102. In another embodiment, the composition further comprises an agent selected from the group consisting of a therapeutic agent, imaging agent, radioactive agent, salt, protein, nucleic acid, gas, and combinations thereof.

Any of the compounds described herein, including compounds (Ia), (Ib), (IIa), (IIb), (IIIa), (IIIb), (IVa) and (IVb), the peptides of sequence selected from SEQ ID NOs:2-13, 15-31, 33-61, 63-102, and any salts thereof, may be synthesized using chemical and biochemical methods known to those skilled in the art of chemical synthesis or peptide synthesis.

Pharmaceutical Compositions and Formulations

The invention also encompasses the use of pharmaceutical compositions of the invention or salts thereof to practice the methods of the invention. Such a pharmaceutical composition may consist of at least one compound or conjugate of the invention or a salt thereof in a form suitable for administration to a subject, or the pharmaceutical composition may comprise at least one compound or conjugate of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular)

form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Methods of the Invention

In one aspect, the compounds of the present invention are useful as protease inhibitors, particularly as inhibitors of cysteine proteases, more particularly as inhibitors of cysteine proteases of the papain superfamily. The present invention includes compositions and formulations comprising the compounds of the invention, including pharmaceutical compositions and formulations comprising the compounds of the invention.

Cysteine protease regulation has a wide range of potential therapeutic applications. For example, the papain family of cysteine proteases are involved in various normal cellular functions and have been implicated in a number of diseases, including cancer (Dumartin, et al., 2011, Cancer Res. 71:7091-7102), neurodegenerative diseases (Schechter & Ziv, 2011, Biol. Chem. 392:555-569), heart disease (Cheng, et al., 2011, Hypertension 58:978-986), viral infection (Bertram, et al., 2011, J. Virol. 85:13363-13372), ischemia/reperfusion injury (Shintani-Ishida & Yoshida, 2011, Biochim. Biophys. Acta 1812:743-751), osteoporosis (Stoch & Wagner, 2008, Clin. Pharmacol. Ther. 83:172-176), and parasite infection (Chandramohanadas et al., 2011, PLoS One 6:e20869).

The present invention includes a method of treating or preventing a disease or condition in a subject in need thereof, wherein the disease or condition is associated with dysfunctional cysteine protease regulation. The method comprises administering to the subject a therapeutically effective amount of a pharmaceutical composition comprising a peptide or peptide-containing moiety, wherein the peptide or peptide-containing moiety comprises any of the compounds described herein, including a peptide selected from the group consisting of SEQ ID NOs:2-13, 15-31, 33-61, 63-102 or a salt thereof, whereby administration of the composition to the subject treats or prevents the disease or condition in the subject.

As contemplated herein, such diseases or conditions may include, without limitation, various infectious diseases, such as SARS, neurological diseases like Alzheimer's, reperfusion injury, or cancer. Other examples of diseases or conditions include infections by *Pneumocystis carinii, Trypsanoma cruzi, Trypsanoma brucei*, and *Crithidia fusiculata*; as well as in schistosomiasis, malaria, tumor metastasis, metachromatic leukodystrophy, muscular dystrophy, amytrophy; diseases of excessive bone or cartilage loss, including osteoporosis, gingival disease including gingivitis and periodontitis, arthritis (including osteoarthritis and rheumatoid arthritis), Paget's disease; hypercalcemia of malignancy, and metabolic bone disease.

Activity-Based Probes

Activity-based probes (ABPs) are used to characterize families or individual active proteases within complex proteomes. ABPs typically possess two main structural components that contribute to their target specificity: (i) a mechanism-based inhibitor scaffold to covalently or non-covalently target catalytic residues or the active site of proteases; and (ii) a reporter tag, such as a fluorophore or biotin, for the visualization, characterization of labeling events, and eventual affinity purification of target proteins.

As contemplated herein, the compounds of the present invention may be used in the construction of ABPs for in vitro, in cell, and in vivo labeling of cysteine proteases. In one embodiment, the ABPs may include amino acid spacers and/or may be tagged, as would be understood by those skilled in the art.

Kits

The present invention includes a kit comprising a compound or composition of the present invention, and an instructional material which describes, for instance, administering the compound or composition to a subject as a therapeutic treatment as described elsewhere herein.

In one embodiment, this kit further comprises a (preferably sterile) pharmaceutically acceptable carrier suitable for dissolving or suspending the therapeutic composition, for instance, prior to administering to a subject. Optionally, the kit comprises an applicator for administering the compound or composition.

Alternatively, the kit may include at least one ABP and instructional material which describes, for instance, procedural steps in completing an assay of a sample including a protease, as described elsewhere herein.

In one embodiment, the present invention includes an assay kit for identification of a protease, such as calpain, in cell lysates and live cell imaging. For example, the kit may include at least one cysteine protease probe and instructions for its use in the identification of protease activity, such as in a disease study, a cell life cycle study or other functional studies. In another embodiment, the probes of the present invention can be used to specifically label their respective activated proteases over unactivated proteins and other cysteine proteases.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Identification of Cysteine Inhibitors and their Selectivity to Papain Family Proteases All papain family proteases have a highly conserved active site cleft. The similarities of these active sites have made the development of specific inhibitors difficult. However, within the papain superfamily, the pro-domains of the cathepsins, and the endogenous inhibitor for Calpain-1 (Calpastatin) contain α-helices, which block the active site and prevent proteolytic cleavage (Hanna, et al., 2008, Nature 456:409-412; Podobnik, et al., 1997, J Mol Biol 271:774-788; Coulombe, et al., 1996, EMBO J 15:5492-5503; Kaulmann et al., 2006, Protein Sci 15:2619-2629), as illustrated in FIG. 1. As contemplated herein, using the natural α-helix alone provides a scaffold for a novel inhibitor class (and probes) that are specific for individual cathepsins and calpains. As demonstrated herein, the use of α-helical mimetics to differentiate amongst cysteine proteases is an unprecedented approach for the development of inhibitors/therapeutics.

The natural small peptides that are α-helical in the context of the larger protein are themselves not likely to inhibit the enzyme due to the overwhelming loss of entropy associated with formation of a secondary structure and then binding to the enzyme. To reduce the energy needed for binding, the helix is stabilized with an appropriate linker (Henchey, et al., 2008, Curr Opin Chem Biol 12:692-697).

Figures 2A, 2B:
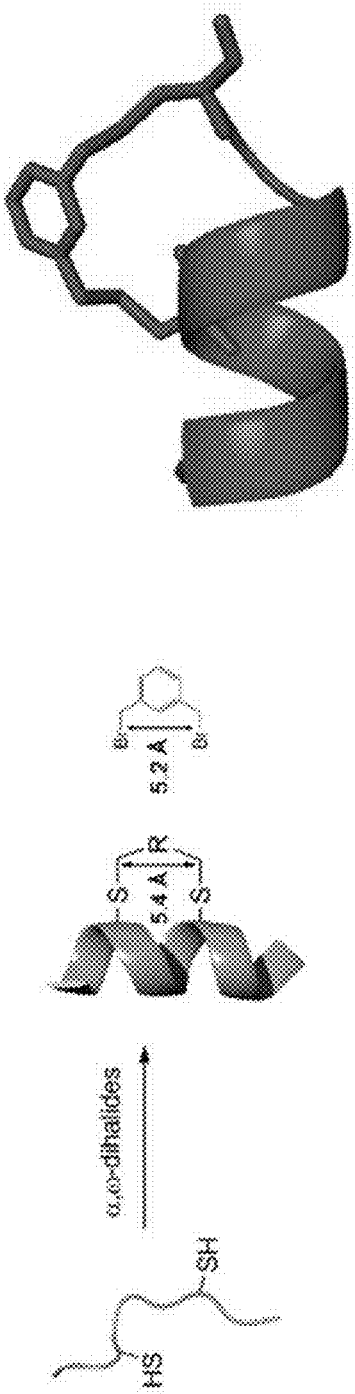
FIGS. 2A-2C, illustrate inhibitors of the present invention.
Figure 2C:
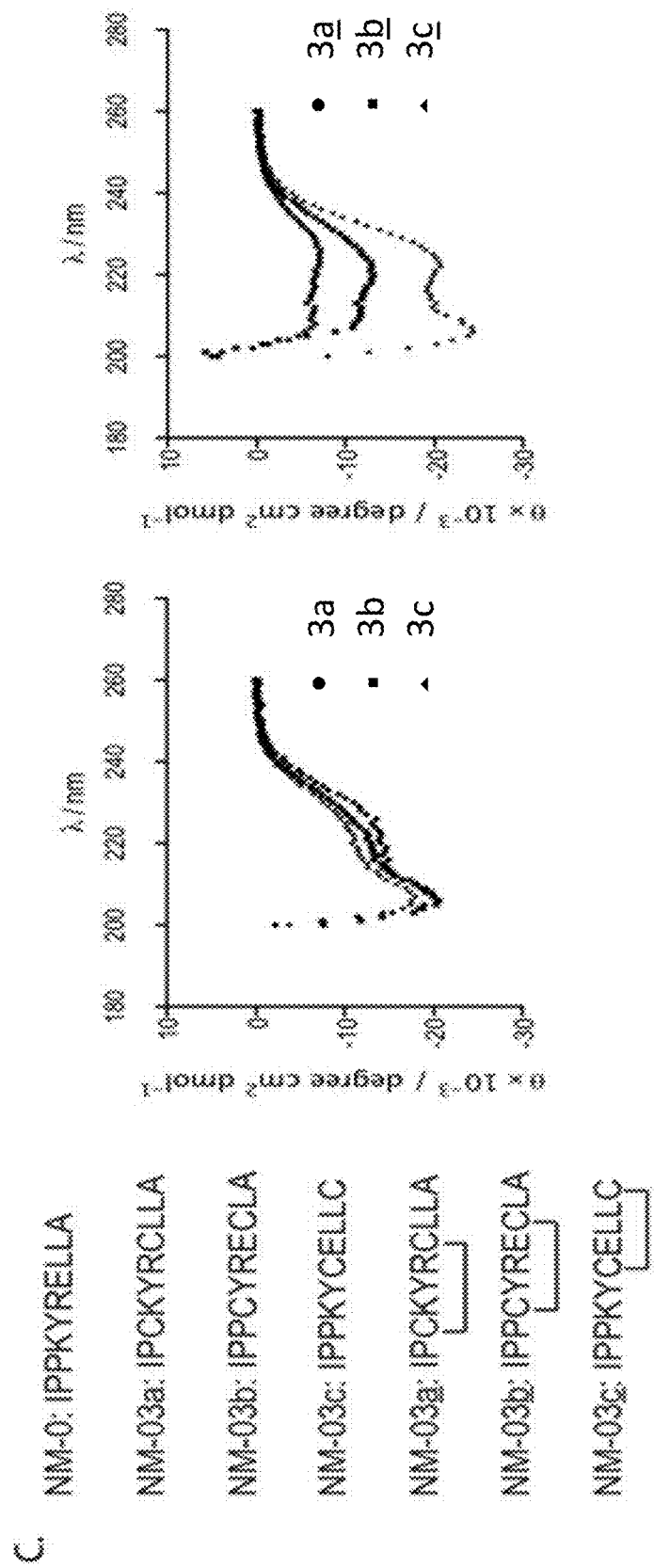
Figure 4A:
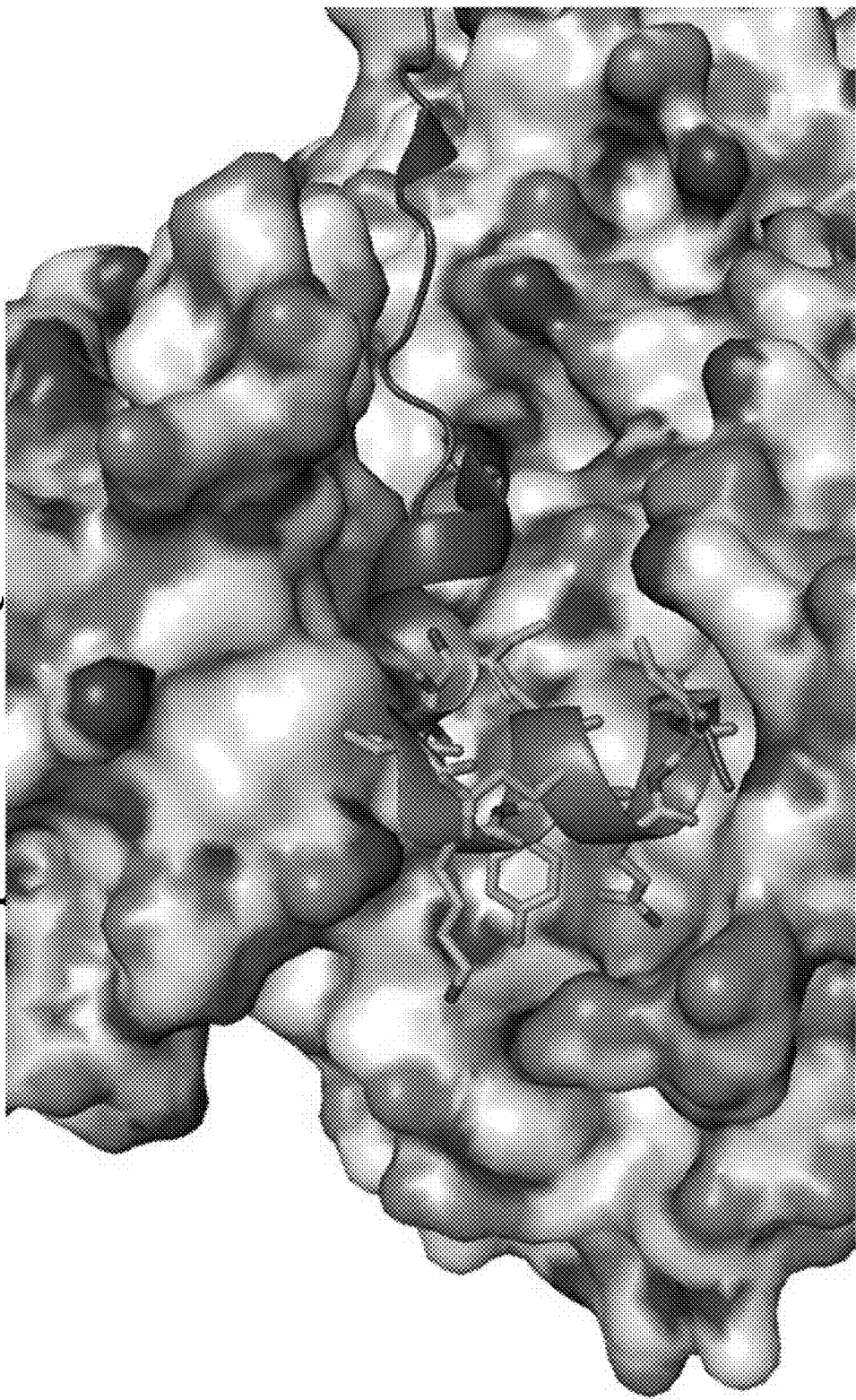
FIGS. 4A-4B, is an illustration of the predicted binding mode of Calpain to inhibitor IPP-KYCEQLC and Cathepsin S to inhibitor WWEWWC-SLMCS.
Figure 4B:
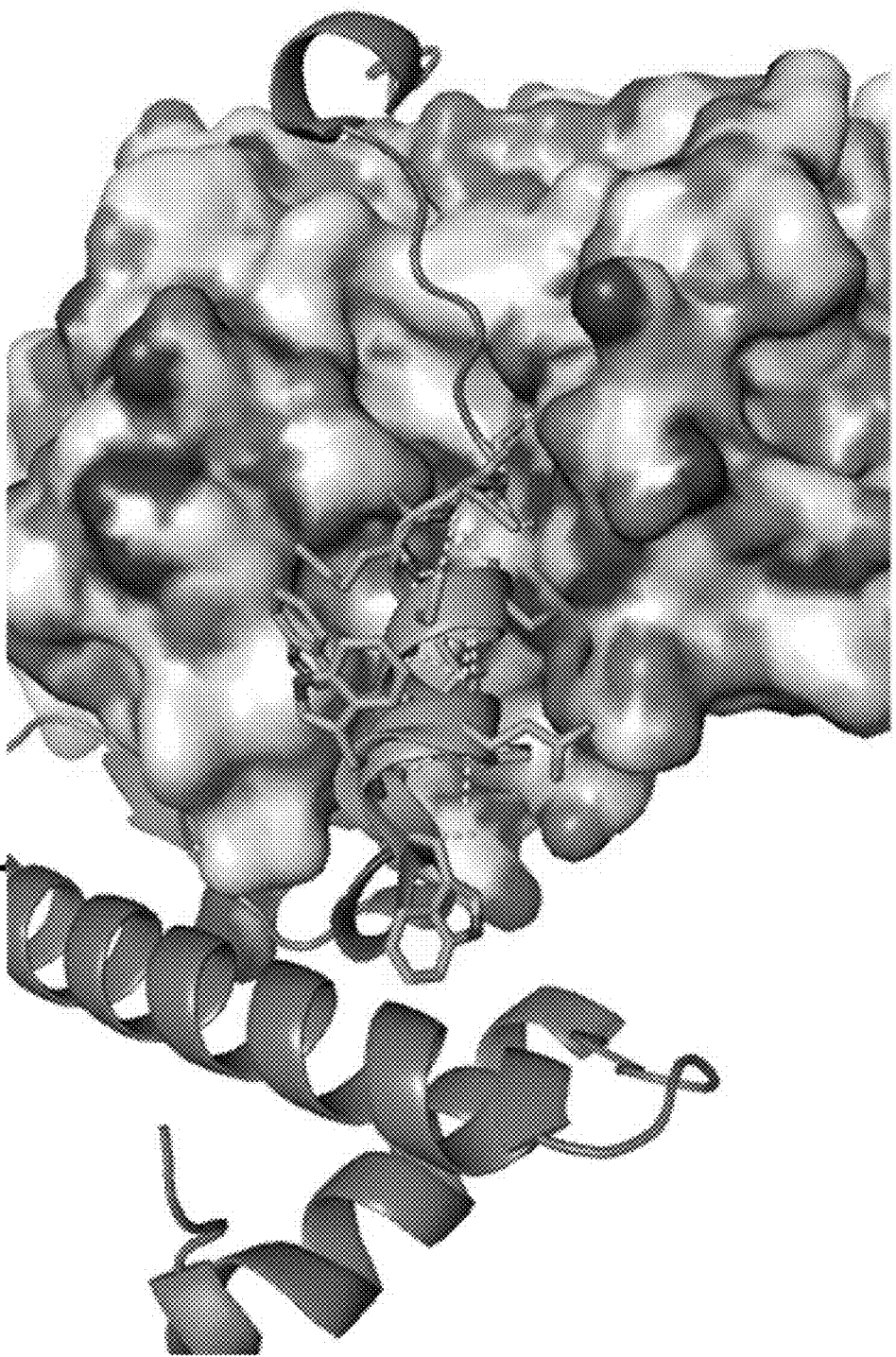
Figure 5C:
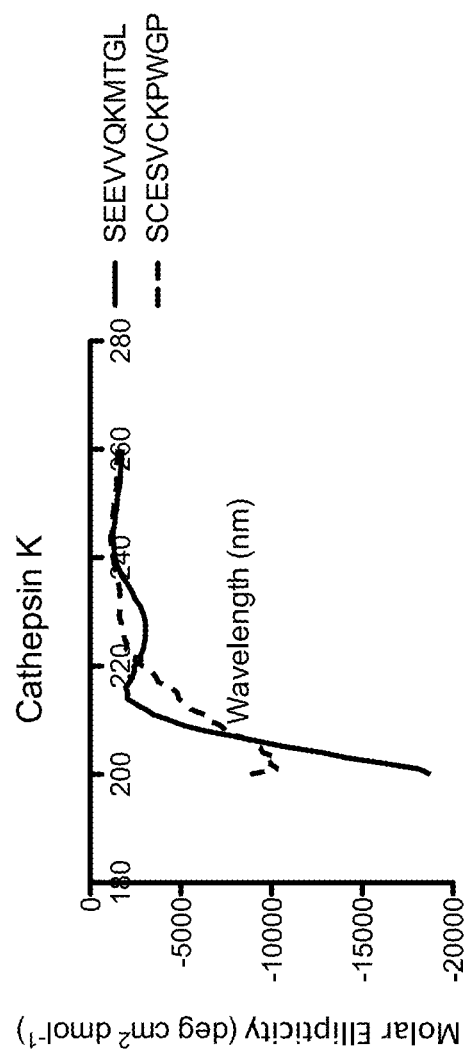
FIG. 5, comprising FIGS. 5A-5C, comprises a set of CD spectra for peptides of the invention. Stabilization of the helix (dotted lines) resulted in a more helical inhibitor, as evidenced by the shift in minima from ~200 nm to 208 and 222 nm. This change in secondary structure suggests that the stabilization reduced the free energy needed for binding resulting in inhibitory activity.
Figure 6:
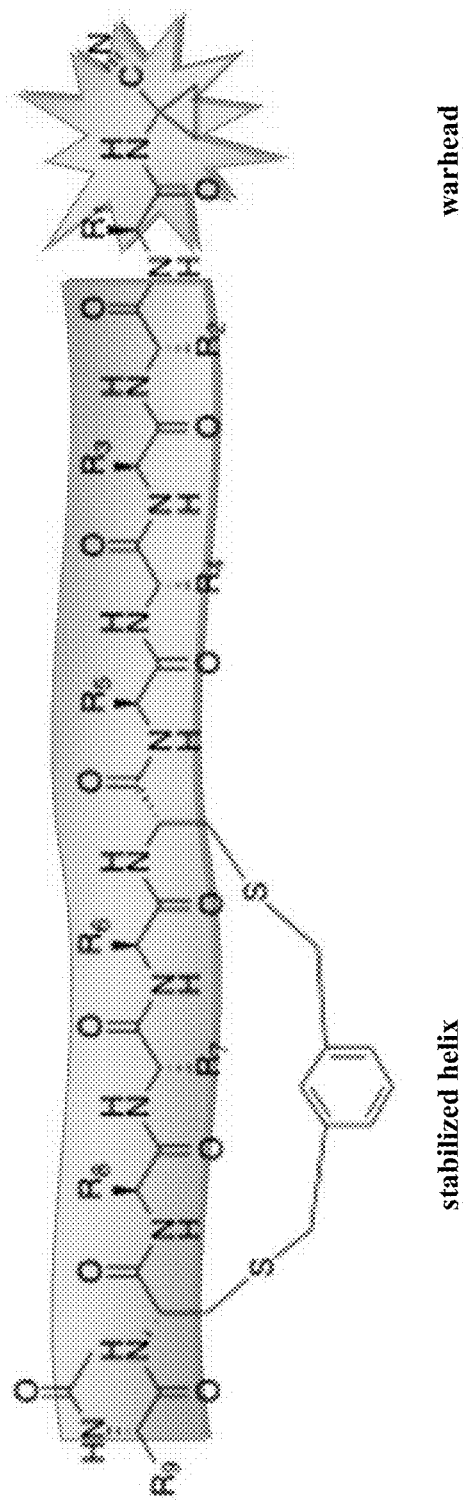
FIG. 6 illustrates a covalent inhibitor contemplated within the invention.

Thus, the present invention includes a series of potent and highly specific α-helical inhibitors for papain family cysteine proteases. For example, as shown in FIG. 2A, the present invention includes potent and highly specific inhibitors for Calpain-1, Cathepsin K, Cathepsin L, and Cathepsin S. The predicted binding mode of Calpain and Cathepsin S are shown in FIG. 4. These short α-helical peptidomimetic inhibitors are modeled after the natural pro-domain sequence but contain a cysteine substitution at specific residues in i,i+4 positions, as shown in FIG. 2B. These cysteine residues are used for stabilization of the helix utilizing an appropriate linker (Muppidi, et al., 2011, Chem Commun (Camb) 47:9396-9398). After synthesis, each inhibitor was tested against its respective protease using an in vitro fluorescence-based assay. For each enzyme, at least one inhibitor was identified that is relatively potent and highly specific for its individual protease. These inhibitors can be modified or otherwise optimized to attain higher potency and selectivity through identification of key interactions between the inhibitor and the active site amino acid residues. Such optimization involves visual examination of the protease crystal structure, and substitution with either non-natural or natural amino acids to exploit possible crucial non-covalent protein ligand interactions, such as hydrogen bond, electrostatic, hydrophobic, and Van der Waals interactions.

Example 2

Activity-Based Probes of Active Proteases

Activity-based probes (ABPs) are used to characterize families or individual active proteases within complex proteomes. ABPs typically possess two main structural components that contribute to their target specificity: (i) a mechanism-based inhibitor scaffold to covalently or non-covalently target catalytic residues or the active site of proteases; and (ii) a reporter tag, such as a fluorophore or biotin, for the visualization, characterization of labeling events, and eventual affinity purification of target proteins.

As contemplated herein, ABPs may be used for in vitro, in cell, and in vivo labeling of cysteine proteases. For example, FIG. 3 illustrates one series of probes for calpains. These probes are comprised of a stabilized α-helix as a specificity element with an epoxysuccinic acid as an electrophilic "warhead" that irreversibly reacts with the active site cysteine, and a biotin, FITC, TAMRA, or BODIPY tag as reporters. To make probes cell permeable, a 7-amino acid (RRMKWKK) version of the cell penetrating peptide, penetratin was added (Fiorino et al., 2007, J Pept Sci 13:70-73).

Figures 3A, 3B:
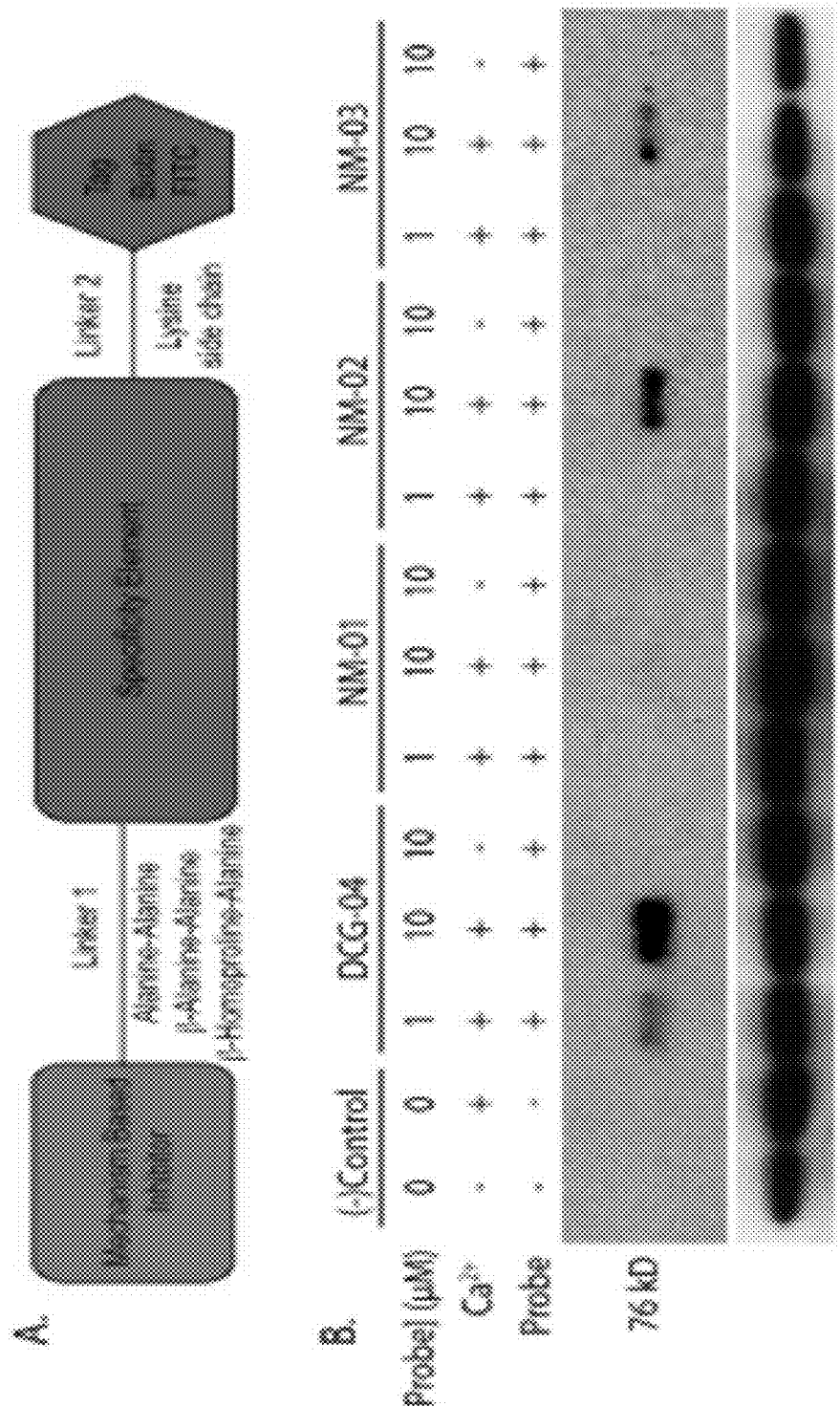
FIGS. 3A-3E, illustrates an activity-based probe and a characterization of protease activity.
Figures 3C, 3D:
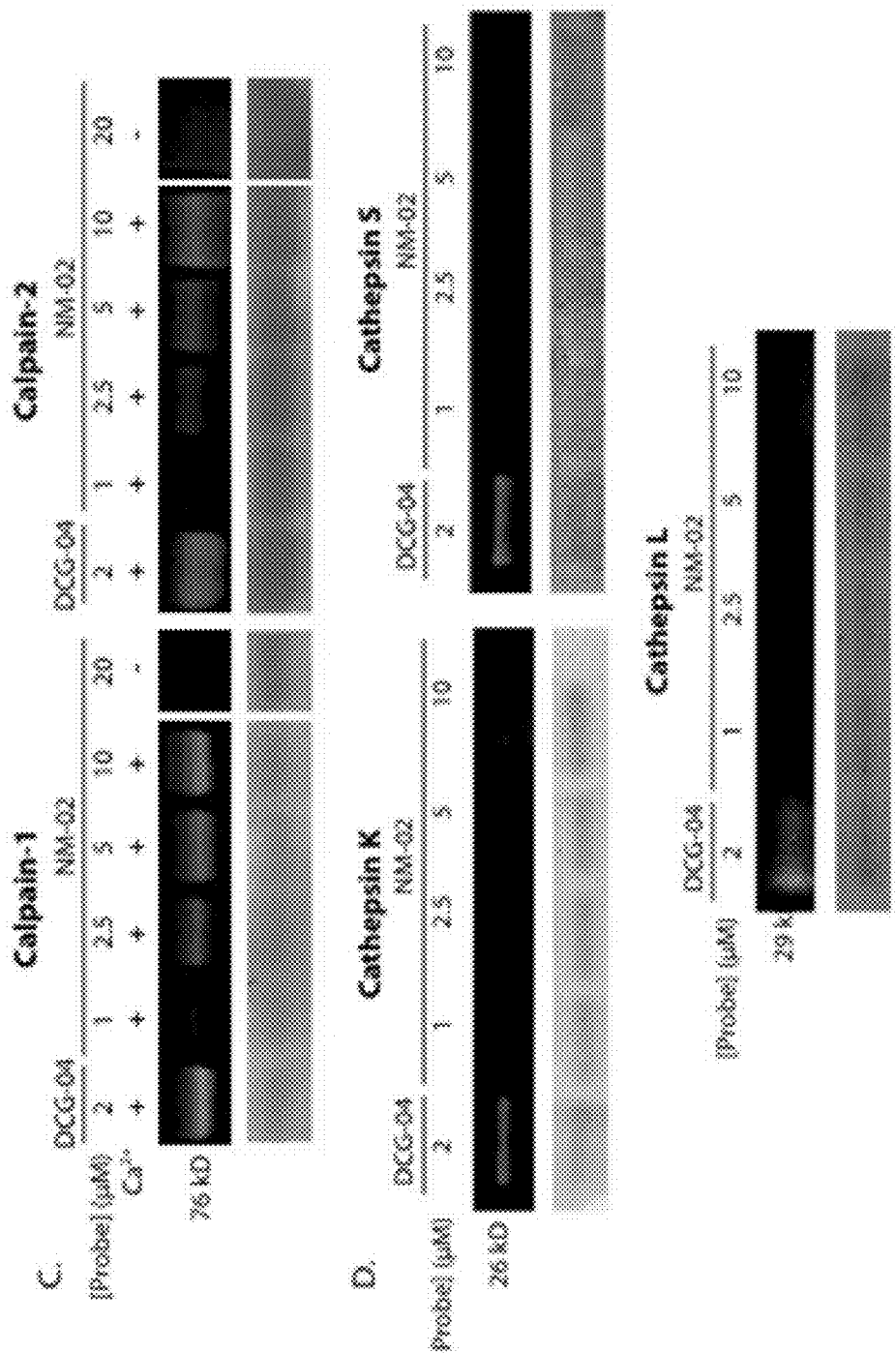
Figure 3E:
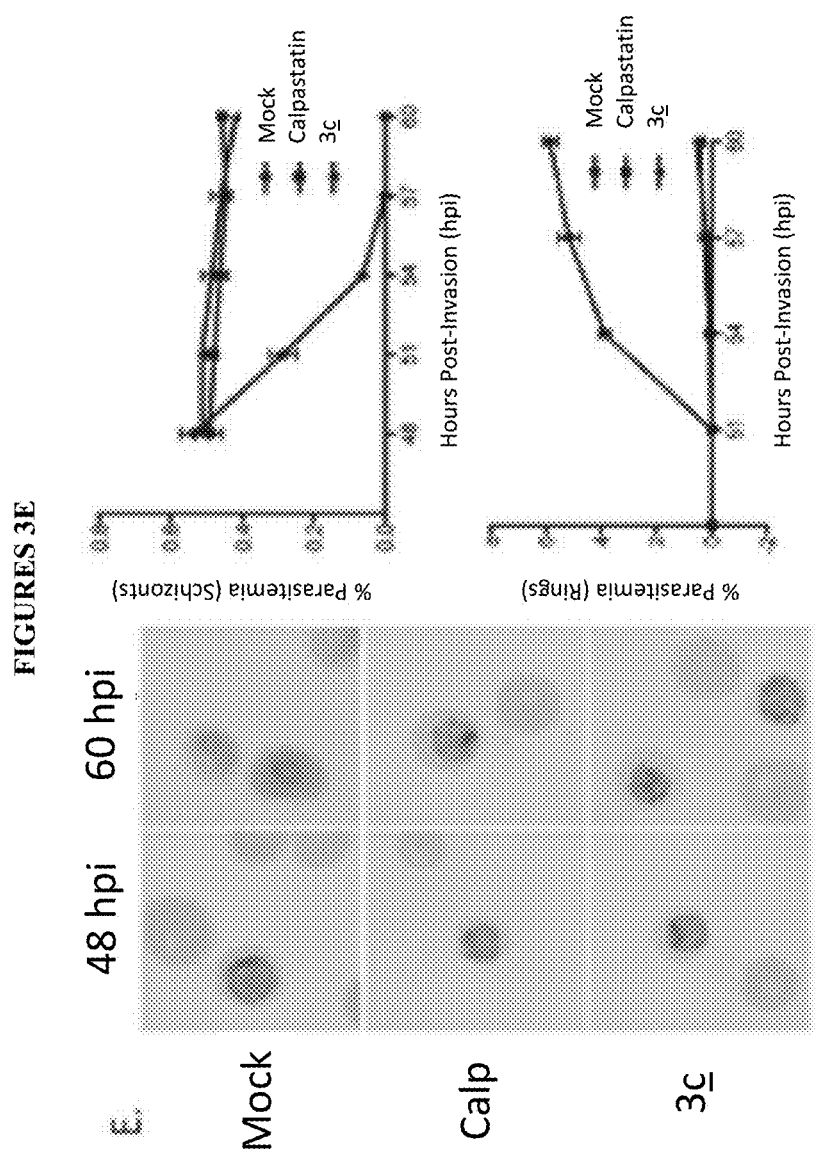

During the development of these ABPs, three different amino acid spacers between the two-turn helical inhibitor and the epoxysuccinic acid were tested. As shown in FIG. 3B, it was found that the β-alanine, alanine spacer was the most potent. Further, FITC tagged versions of the activity-based probe were also synthesized and tested with the β-alanine, alanine spacer against purified Calpain-1 and Calpain-2, Cathepsin K, Cathepsin L, and Cathepsin S. As demonstrated in FIGS. 3C and 3D, the probe only labels active Calpain-1 or -2, but not unactivated Calpain, Cathepsin K, Cathepsin L or Cathepsin S. The most potent calpain inhibitor was also tested on Plasmodium falciparum infected red blood cells, and as shown in FIG. 3E, it was found that the inhibitor works similarly to the endogenous inhibitor calpastatin.

As contemplated herein, the probes of the present invention may be tested on live mouse embryo fibroblast (mEF) wild type and small subunit knockout cells, with and without calcium. Further, protease function in post ischemic injury in rat hippocampal slices may also be tested in light of the compounds and methods of the present invention.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising a peptide, or a salt thereof, wherein said peptide or salt thereof comprises at least one α-helix and the amino acid sequence selected from the group consisting of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 76, SEQ ID NO: 77, SEQ ID NO: 78, SEQ ID NO: 80, SEQ ID NO: 82, SEQ ID NO: 83, SEQ ID NO: 84, SEQ ID NO: 85, SEQ ID NO: 86, and SEQ ID NO: 88, wherein each amino acid sequence comprises at least two cysteine residues that are covalently connected through an alpha,alpha'-meta-xylylene linker; and wherein the peptide inhibits a cysteine protease comprising calpain.

2. The composition of claim 1, wherein the peptide further comprises a covalent modifying group added to the N-terminus of the peptide, wherein the covalent modifying group comprises a nitrile, alpha beta unsaturated ketone, vinyl sulfone, or acyloxymethyl ketone.

* * * * *